US008639579B2

(12) United States Patent
Kalevik et al.

(10) Patent No.: US 8,639,579 B2
(45) Date of Patent: Jan. 28, 2014

(54) SYSTEM AND METHOD FOR MANAGING REQUESTS FOR MEDICAL TRANSPORTATION

(75) Inventors: Mark Kalevik, Aurora, CO (US); Tom Coogan, Erie, CO (US); Denis Jackson, Discovery Bay, CA (US); Glenn Leland, Larkspur, CO (US); Steve Murphy, Ft. Lauderdale, FL (US); Kathy Wiljanen, Des Moines, IA (US); Mark Rector, Littleton, CO (US)

(73) Assignee: American Medical Response, Englewood, CO (US)

( * ) Notice: Subject to any disclaimer, the term of this patent is extended or adjusted under 35 U.S.C. 154(b) by 2723 days.

(21) Appl. No.: 10/771,178

(22) Filed: Feb. 2, 2004
(Under 37 CFR 1.47)

(65) Prior Publication Data
US 2005/0038696 A1 Feb. 17, 2005

(51) Int. Cl.
*G06Q 20/00* (2012.01)
(52) U.S. Cl.
USPC ............ 705/20; 600/300; 705/2; 705/3
(58) Field of Classification Search
USPC ................... 705/20, 3, 2; 600/300
See application file for complete search history.

(56) References Cited

U.S. PATENT DOCUMENTS

| | | | |
|---|---|---|---|
| 5,471,382 A * | 11/1995 | Tallman et al. | 600/300 |
| 5,508,912 A * | 4/1996 | Schneiderman | 705/3 |
| 5,761,278 A | 6/1998 | Pickett et al. | |
| 6,076,065 A | 6/2000 | Clawson | |
| 6,078,894 A | 6/2000 | Clawson et al. | |
| 6,106,459 A | 8/2000 | Clawson | |
| 6,117,073 A * | 9/2000 | Jones et al. | 600/300 |
| 6,118,866 A | 9/2000 | Shtivelman | |
| 6,198,914 B1 * | 3/2001 | Saegusa | 455/404.2 |
| 6,415,018 B1 | 7/2002 | Antonucci et al. | |
| 6,523,009 B1 * | 2/2003 | Wilkins | 705/3 |
| 6,607,481 B1 | 8/2003 | Clawson | |
| 6,868,386 B1 * | 3/2005 | Henderson et al. | 705/4 |
| 7,233,905 B1 * | 6/2007 | Hutton et al. | 705/2 |
| 8,090,598 B2 * | 1/2012 | Bauer et al. | 705/4 |
| 8,396,191 B2 * | 3/2013 | Clawson | 379/45 |
| 2007/0203742 A1 * | 8/2007 | Jones et al. | 705/2 |

* cited by examiner

*Primary Examiner* — Lena Najarian
*Assistant Examiner* — Teresa Woods
(74) *Attorney, Agent, or Firm* — Foley & Lardner LLP

(57) ABSTRACT

A call center for handling requests for medical transportation utilizes a system that assists a call center agent by automatically determining, or prompting the agent to ask for, all information needed to assess the level of service required and the effects of any applicable contractual provisions. The system captures information relating to the patient and the requested transportation, and applies service level rules representing the applicable regulatory requirements for medical transportation at the location of the patient to determine the required level of service based on the patient's condition and needs. The system further applies business rules representing the contractual provisions that are applicable to the requested transportation to determine responsibility for the cost of transportation, the authority of the requester to change the level of service or other aspects of the transportation, and the responsibility for the cost of transportation in the event that an aspect of the transportation has been changed.

7 Claims, 23 Drawing Sheets

| Diagnosis Description | Diagnosis Code | ICD | Severity Level |
|---|---|---|---|
| Abdominal Aortic Aneurysm | AbdominalAorticAneurysm | 441.4 | Very Acute |
| Abdominal Distention | AbdominalDistention | 787.3 | Non-Acute |
| Abdominal Pain, Acute | AbdominalPainAcute | 789.0 | Acute |
| Abnormal EKG | Abnormal EKG | | Acute |
| Abortion | Abortion | 637.9 | Non-Acute |
| Abruptio Placentae | AbruptioPlacentae | 641.2 | Very Acute |
| Abscess | Abscess | 682.9 | Non-Acute |
| Achalasia | Achalasia | 530.0 | Non-Acute |
| Acne | Acne | 706.1 | Non-Acute |
| Acquired Immune Deficiency Syndrome | AcquiredImmuneDeficiencySyndrome | 042 | Chronic |

Figure 17

| User Interface String | Level of Service | Equipment Code |
|---|---|---|
| Suction | BLS | Suction |
| Heavy Duty Stretcher / Pram (>300lbs) | Not authorized | HDutySuction |
| IV | BLS | IV |
| IV pump | BLS | IVPump |
| Oxygen | Not authorized | O2 |
| Oxygen (Nasal Cannula) | Not authorized | O2Cannula |
| Oxygen (Rebreather / NonRebreather) | BLS | O2NonReBreather |
| Oxygen (PEEP) | ALS | O2Peep |
| DNR/CPR directive | Not authorized | DNR |
| Arterial sheath | CCT | ArtialSheath |
| Balloon pump | CCT | BallPump |
| Stretcher / pram | Not authorized | Pram |

Figure 18

| Classification | Name of Medication | Level of Service | IV Push | IV Pump | IV Drip | P.C.A. | E.T | Nebu-izer | S.L. | I.M. | SQ | P.O. | Tube Feeding |
|---|---|---|---|---|---|---|---|---|---|---|---|---|---|
| Antibiotic | Antibiotics | None | N/A | N/A | N/A | N/A | N/A | N/A | N/A | N/A | N/A | N/A | N/A |
| Antifungal | Antifungals | None | N/A | N/A | N/A | N/A | N/A | N/A | N/A | N/A | N/A | N/A | N/A |
| Antiviral | Antivirals | None | N/A | N/A | N/A | N/A | N/A | N/A | N/A | N/A | N/A | N/A | N/A |
| Cardiovascular | Adensosine (Adenocard) | Variable | ALS | CCT | CT | N/A | N/A | N/A | N/A | N/A | N/A | N/A | N/A |
| Cardiovascular | Amrinone (Inocor) | CCT | CCT | CCT | CCT | N/A | N/A | N/A | N/A | N/A | N/A | N/A | N/A |
| Cardiovascular | Atropine | Variable | ALS | N/A | N/A | N/A | ALS | N/A | N/A | N/A | N/A | N/A | N/A |
| Cardiovascular | Bretylium | Variable | ALS | ALS | ALS | N/A | N/A | N/A | N/A | N/A | N/A | N/A | N/A |
| Cardiovascular | Digoxin | Variable | CCT | CCT | CT | N/A | N/A | N/A | N/A | N/A | N/A | N/A | N/A |
| Cardiovascular | Dilliazem | CCT | CT | CCT | CT | N/A | N/A | N/A | N/A | N/A | N/A | N/A | N/A |
| Cardiovascular | Dopamine | Variable | ALS | ALS | ALS | N/A | N/A | N/A | N/A | N/A | N/A | N/A | N/A |

Figure 19

| Response Location Facility Type | Response Area | Destination Location Facility Type | Destination Area | Diagnosis Severity Level | Original Transaction Classification | Response Time Description (Original) |
|---|---|---|---|---|---|---|
| Ambulatory Surgery Care | ANY | Acute care | ICU OR MICU OR SICU | NOT 911 AND NOT Very Acute | Scheduled | Immediate |
| Ambulatory Surgery Care | ANY | Acute care | Telemetry | NOT 911 AND NOT Very Acute | Scheduled | Immediate |
| Ambulatory Surgery Care | ANY | Acute care | Floor, Specialty, Room OR Bed | NOT 911 | Scheduled | Scheduled |
| Ambulatory Surgery Care | ANY | Acute care | Lobby OR Admissions | NOT 911 | Scheduled | Scheduled |
| Urgent Care | ANY | Acute care | Emergency | Very acute | Scheduled | Urgent |
| Urgent Care | ANY | Acute care | Emergency | 911 | ANY | 911 |
| Urgent Care | ANY | Acute care | PICU OR NICU | Very acute | Scheduled | Urgent |
| Urgent Care | ANY | Acute care | CU OR MICU OR SICU | Very acute | Scheduled | Urgent |
| Urgent Care | ANY | Acute care | Telemetry | Very acute | Scheduled | Urgent |

Figure 20

| IF Response location Facility Type | AND Destination location Facility Type | THEN |
|---|---|---|
| Acute care | Acute Care | run Plan Type rules |
| Acute care | Ambulatory Surgery Center, Skilled Care Facility, Clinic Specialty Care, Clinic Medical Center, Mental Health Facility OR Urgent Care | use Level of Service |
| Acute care | Specialty Clinic, Hospice OR Airport | Non scheduled |
| Acute care | Nursing Home Non Skilled, Office or Business OR Private Residence | Non scheduled |
| Ambulatory Surgery Center, Skilled Care Facility, Clinic Specialty Care, Clinic Medical Center, Mental Health Facility OR Urgent Care | Ambulatory Surgery Center, Skilled Care Facility, Clinic Specialty Care, Clinic Medical Center, Mental Health Facility OR Urgent Care OR Veterans Administration | use Level of Service |
| Specialty Clinic, Hospice OR Airport | Specialty Clinic, Hospice OR Airport | use Level of Service |
| Nursing Home Non Skilled, Office or Business OR Private Residence | Nursing Home Non Skilled, Office or Business OR Private Residence | Non scheduled |
| Ambulatory Surgery Center, Skilled Care Facility, Clinic Specialty Care, Clinic Medical Center, Mental Health Facility, Urgent Care OR Veterans Administration | Acute Care | run Plan Type rules |

Figure 21

| Plan Type (Response Location) | Contract Type (Response Location) | Plan Type (Destination Location) | Contract Type (Destination Location) | THEN |
|---|---|---|---|---|
| In Plan | Owned | In Plan | Owned | use Level of Service |
| In Plan | Contracted | In Plan | Contracted | use Level of Service |
| Out of Plan | Contracted | Out of Plan | Contracted | Non Scheduled |
| Out of Plan | Non Contracted | Out of Plan | Non Contracted | Non Scheduled |
| In Plan | Owned | In Plan | Contracted | use Level of Service |
| In Plan | Owned | Out of Plan | Contracted | use Level of Service |
| In Plan | Owned | Out of Plan | Non Contracted | use Level of Service |
| In Plan | Contracted | In Plan | Owned | use Level of Service |
| In Plan | Contracted | Out of Plan | Contracted | use Level of Service |

Figure 22

| Name | Code | Reference ID Code | Affiliated Member | Affiliated RN | Affiliated MD | Affiliated Associate | Non-Affiliated Member | Non-Affiliated RN | Non-Affiliated MD | Non-Affiliated Associate |
|---|---|---|---|---|---|---|---|---|---|---|
| Kaiser CO Springs, Member Access | KCoSpgsMem | CA | Yes | Yes | Yes | Associate | Yes | Yes | Yes | Associate |
| Kaiser Denver, Member Access | KDenMem | CB | Yes | Yes | Yes | Yes | Yes | Yes | Yes | Yes |
| Humana Florida, Member Access | HumFiMem | FA | Yes | Yes | Yes | Yes | No | No | No | Yes |
| Kaiser Hawaii, Ext. Provider | KHIExtProv | HA | Yes | Yes | Yes | No | No | No | No | No |
| Kaiser Hawaii, Staff Provider | KHawStaff | HB | Yes | Yes | Yes | No | No | No | Yes | No |
| Kaiser Hawaii, RN / Member Access | KHIRNMem | HC | Yes | Yes | Yes | Yes | Yes | Yes | Yes | Yes |

Figure 23

| Original Transaction Classification | L.O.S. Change | L.O.S. Change Reason | Response Time Description Change | Response Time Change Reason | Response Time Interval Change | Final Transaction Classification | Final Transaction Classification Change Type |
|---|---|---|---|---|---|---|---|
| Scheduled | Downgrade | Physician (Clinical) | 911 Upgrade | Client | No Change | Non-Scheduled 911 | L.O.S.Downgrade / R.T.Upgrade |
| Scheduled | Downgrade | Physician (Clinical) | Downgrade | Client | No Change | Scheduled | LOS. Downgrade/ R.T Downgrade |
| Scheduled | No Change | No Change | Downgrade | Client | No Change | Scheduled | R.T. Downgrade |
| Scheduled | No Change | No Change | 911 Upgrade | Client | No Change | Non-Scheduled 911 | R.T. Upgrade 911 |
| Scheduled | No Change | No Change | No Change | Client | 911 Upgrade | Non-Scheduled 911 | R.T. Upgrade 911 |
| Scheduled | Downgrade | Physician (Clinical) | Downgrade | Client | No Change | Scheduled | LOS. Downgrade / R.T Downgrade |
| Scheduled | Downgrade | Physician (Clinical) | No Change | No Change Requested | No Change | Scheduled | L.O.S. Downgrade |
| Scheduled | Downgrade | Physician (Clinical) | Upgrade | Client | No Change | Scheduled | LOS. Downgrade / R.T. Upgrade |
| Scheduled | No Change | No Change | Downgrade | Client | No Change | Scheduled | R.T. Downgrade |
| Scheduled | No Change | No Change | 911 Upgrade | Client | No Change | Non-Scheduled 911 | R.T. Upgrade 911 |
| Scheduled | No Change | No Change | No Change | Client | 911 Upgrade | Non-Scheduled 911 | R.T. Upgrade 911 |
| Scheduled | No Change | Physician (Clinical) | No Change | No Change Requested | No Change | Scheduled | No Change |

SYSTEM AND METHOD FOR MANAGING REQUESTS FOR MEDICAL TRANSPORTATION

RELATED APPLICATIONS

This application claims priority from PCT application PCT/US02/24473, filed 2 Aug. 2002, which claims priority from U.S. provisional patent application Ser. No. 60/309,534, filed 2 Aug. 2001, the entirety of which are incorporated herein by reference.

BACKGROUND OF THE INVENTION

1. Field of the Invention

The present invention relates to systems and methods for managing requests for medical transportation.

2. Description of the Related Art

Requests for medical transportation, such as ambulance transportation, are typically handled by agents at a call center who determine the type of service required, an appropriate transportation provider to handle the request, and an assignment of liability for the cost of transportation. These decisions require consideration of a wide range of factors.

Each request for medical transportation involves the interests of many different stakeholders. The patient requires transportation that addresses his medical needs in a timely manner, and for which the cost is preferably born by the patient's insurer. Depending on the circumstances, the transportation request may be made by a patient or by attending medical personnel such as a nurse or physician. In such a case the medical personnel may require transportation to be provided in accordance with their assessment of the patient's needs, and in a manner that minimizes the costs born by the entity that employs them.

The patient's insurer has an interest in ensuring that transportation is provided in the most cost effective manner, and is provided in accordance with its obligations to the patient. The patient's insurer may also have agreements in place with one or more transportation providers governing the circumstances under which that provider will be used, mandating aspects of transportation such as response time, and the governing manner in which the cost of transportation is determined under various scenarios (e.g. fixed fee vs. at cost). The transportation provider has an interest in handling only those requests for which costs can be recovered.

Various governmental bodies at the local, regional and national levels are also stakeholders. These bodies have interests in protecting the populace at large, which is achieved through regulations that mandate minimum levels of service under various transportation scenarios. Where a governmental body is also the insurer of the patient (as in the case of Medicare coverage), further regulations may govern authorized services and cost and billing arrangements.

While the aforementioned stakeholders (patient, physician/nurse, insurer, transportation provider) are typically distinct entities, in some instances certain stakeholders may be affiliated with other related parties. For example, an insurer may own a facility to which a patient is to be transported to or from, in which case a distinct set of operating rules may apply. A transportation provider may likewise own, be owned by, be jointly owned with, or contract with a call center operator.

Therefore, while it is desirable to utilize a call center to receive and dispatch requests for medical transportation, the agents staffing the call center must be aware of and able to apply all of the contractual and regulatory provisions that are relevant to the circumstances of each request in order to accurately determine patient eligibility for the requested transportation, an appropriate level of service and response time, liability for the cost of transportation, and an appropriate transportation provider. However, due to the many considerations involved in these decisions, the conventional call center agent is typically provided with only a limited set of standard questions to ask every caller, and is trained to determine only an appropriate level of service based on the answers to those questions, or in some instances to determine a level of service and response time, and to assess financial responsibility for the transportation. Even with this reduction of complexity, agent training is difficult and time consuming, and the agent's decisions are prone to error. Further, it is likely that an agent who is in doubt as to the appropriate level of service will opt for the higher of two possible levels of service, sometimes leading to unnecessary over-utilization of scarce and costly resources. These problems are compounded where the requests handled by the agent may originate from different localities governed by different regulations, or may involve the patients of a number of different health insurance providers, thus requiring the agent to apply different sets of rules depending on such factors.

SUMMARY OF THE DISCLOSURE

Various embodiments in accordance with the present invention relate to an automated system for guiding a call center agent in the handling of a request for medical transportation. In accordance with these embodiments, an agent interacts with a computer system that assists the agent by automatically determining, or prompting the agent to ask for, all information needed to assess the level of service required and the effects of any applicable contractual provisions. The system captures information relating to the patient and the requested transportation, and applies service level rules representing the applicable regulatory requirements for medical transportation at the location of the patient to determine the required level of service based on the patient's condition and needs. The system further applies business rules representing the contractual provisions that are applicable to the requested transportation to determine responsibility for the cost of transportation, the authority of the requester to change the level of service or other aspects of the transportation, and the responsibility for the cost of transportation in the event that an aspect of the transportation has been changed.

Two important objectives are served by systems in accordance with the invention. One objective is to optimize the utilization of medical transportation resources. Through the application of service level rules that reflect the regulations governing medical transportation at the location of the patient, the system ensures that the call center agent acquires the information necessary to determine the clinically appropriate level of service, and that the correct determination is made. In addition, through the application of business rules representing the various contractual provisions applicable to the patient, the patient's insurer, and other parties such as facilities and transportation providers, the system is enabled to correctly determine whether changes such as a requested increase in the service level are permitted by the agreements among the relevant parties. Thus the call center agent is assisted to avoid erroneous decisions that result in insufficient transportation service or over-utilization and misallocation of transportation resources.

A second objective is to provide call center agents with "local literacy" in the handling of requests for transportation. By taking account of the location of the patient, and through the use of a body of service level rules that account for all location-specific factors and exceptions, the call center agent may be prompted by the system to elicit from a caller all information that is necessary for making a correct service level determination. Through the use of a body of business rules that represent the contractual provisions applicable to the patient at issue, that patient's insurer, and related parties such as facilities and transportation providers, the call center agent is enabled to elicit all necessary information and may be provided with correct determinations concerning issues such as responsibility for the cost of transportation, authority of a caller to change the service level or other aspects of the transportation, responsibility for the cost of transportation in the event of such a change, and other issues such as the manner in which cost is assessed or the use of required transportation service providers. By supplying this expertise in an automated manner, the call center agent is enabled to make correct decisions despite the applicability of a large number of differing considerations to each call. This enables centralization of call center services without degrading the quality of service.

While a preferred embodiment of the invention for achieving these objectives is described herein, the preferred embodiment merely represents one of many possible implementations in accordance with the invention. In general terms, the invention is characterized by a system comprising a body of service level rules and business rules that represent the service level regulations and contractual provisions, respectively, that are applicable to requests for transportation originating from geographic locations served by a call center, and more particularly from patients and facilities served by the call center. The system engages in an interactive process through which information is obtained from callers such as patients or other persons requesting transportation on a patient's behalf, and the service level and business rules are applied to the information so obtained to make one or more determinations that are relevant to formulating an appropriate request for transportation. Among the determinations that may be made by the system are an appropriate level of service, an appropriate response time or other measure of performance mandated by contractual provisions, the eligibility of the patient for transportation under the patient's health insurance plan, a determination of responsibility for the cost of transportation, a determination of authority of the caller to change a service level or other feature of transportation determined by the system, a final determination of responsibility for the cost of transportation in the event that the service level or other feature is changed, and one or more transportation providers to whom the request may be dispatched.

The invention is preferably implemented in a call center model in which a system for processing information in accordance with rules as described above is deployed to assist call center agents in their interaction with callers. In the preferred embodiment, initial information is obtained from callers by a call management application of the system that answers calls and prompts callers to enter information such as an insurance plan member using the telephone keypad. The remainder of the interaction with the caller is then handled by a call center agent. The system provides a series of user interfaces to the call center agent that prompt the call center agent to elicit specific information from the caller, and provides information and determinations as described above based on the information entered by the call center agent.

BRIEF DESCRIPTION OF THE DRAWINGS

Embodiments of the invention may be understood from the following description with reference to the following figures, in which:

FIG. 6 is a view of a graphical user interface displayed by a location module of the preferred embodiment.

FIG. 8 is a view of a graphical user interface displayed by a patient information module of the preferred embodiment.

FIG. 9 is a view of a graphical user interface displayed by a service level determination module of the preferred embodiment.

FIGS. 10a, 10b, 10c and 10d are views of graphical user interfaces displayed by the system for service level determination in the preferred embodiment.

FIG. 10e is a view of a graphical user interface displayed by the system regarding the stability of the patient, according to an exemplary embodiment.

FIG. 11 is a view of a graphical user interface displayed by a schedule module of the preferred embodiment.

FIGS. 12a, 12b and 12c are views of graphical user interfaces displayed by the schedule module for scheduling daily, weekly, or monthly trips in the preferred embodiment.

FIG. 13 is a view of a graphical user interface displayed by a service provider module of the preferred embodiment.

FIG. 14 is a view of a graphical user interface displayed by a send call module of the preferred embodiment.

FIG. 16 is an excerpt of a diagnosis rules table of the preferred embodiment.

FIG. 17 is an excerpt of an equipment rules table of the preferred embodiment.

FIG. 18 is an excerpt of a medications rules table of the preferred embodiment.

FIG. 19 is an excerpt of an original transaction classification rules table of the preferred embodiment.

FIG. 20 is an excerpt of a facility type rules table of the preferred embodiment.

FIG. 21 is an excerpt of a plan type rules table of the preferred embodiment.

FIG. 22 is an excerpt of an authorization rules table of the preferred embodiment.

FIG. 23 is an excerpt of a final transaction classification rules table of the preferred embodiment.

DETAILED DESCRIPTION OF PREFERRED EMBODIMENTS

In the following description, details of a preferred embodiment of the present invention are set forth. However, it will be apparent to those of ordinary skill in the art that alternative embodiments of the invention may be implemented using only some of the features of the preferred embodiment. While various operations may be described herein in a particular order and as discrete tasks, the order of description should not be construed to imply that the tasks involved in those operations must be performed in the order in which they are presented or that those tasks must be performed discretely. Further, in some instances, well known features are omitted or simplified in order not to obscure description of the invention. In this description, the use of phrases such as "an embodiment," "embodiments," "preferred embodiments" and so forth do not necessarily refer to the same embodiment or all embodiments, although they may.

System Overview

Figure 1:
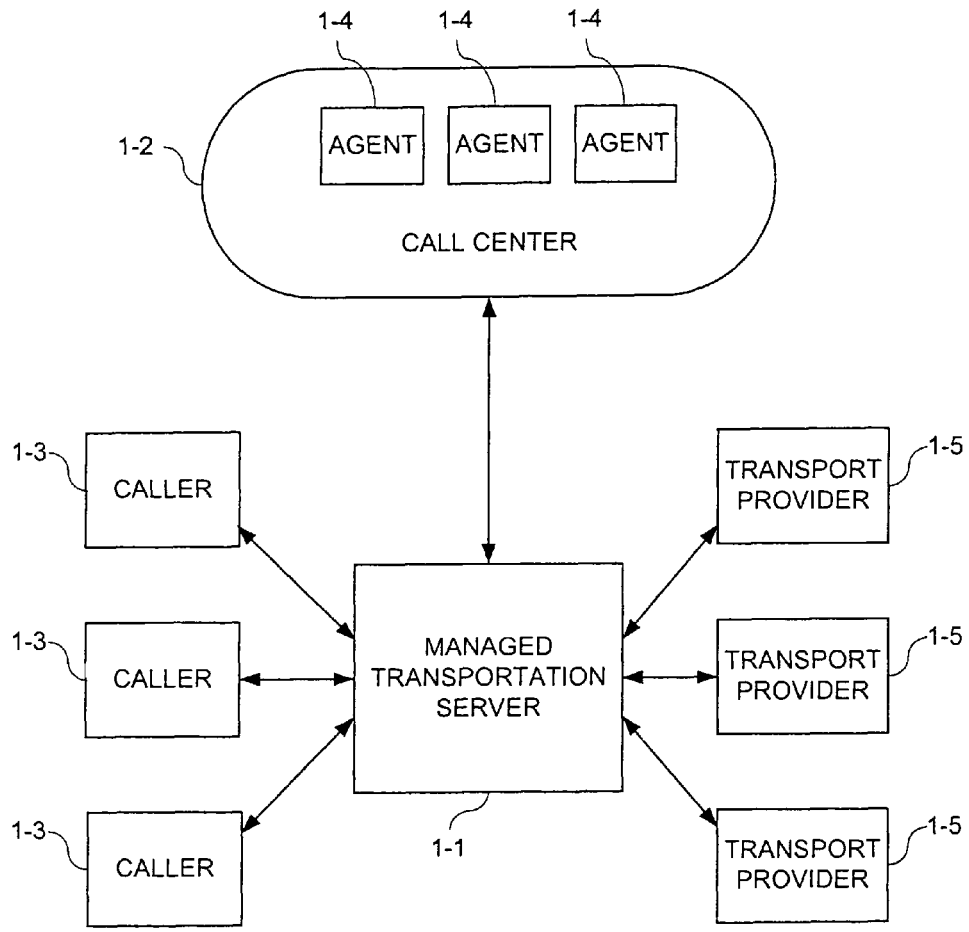
FIG. 1 is a generalized schematic view of a managed transportation system incorporating an embodiment of the present invention.

FIG. 1 shows a generalized diagram of a managed transportation system for handling requests for medical transportation in accordance with a preferred embodiment of the invention. The system includes a managed transportation server 1-1 that is linked to a call center 1-2. The managed transportation server receives calls from callers 1-3 requesting medical transportation for themselves or on behalf of others. The call center 1-2 is staffed by one or more agents 1-4 who interact with the callers. The managed transportation server 1-1 is further linked to transportation providers 1-5 to whom requests for transportation are dispatched by the agents.

During the course of a call, the managed transportation server 1-1 generates graphical user interfaces that are displayed to the agent 1-4 handling the call. The user interfaces prompt the agent to elicit specific information from the caller and enable the agent to enter the elicited information into the system. The user interfaces also display determinations made by the system based on the elicited information, such as the patient's eligibility for service, the level of service and response time that are appropriate for the patient's particular circumstances, determination of responsibility for the cost of transportation, and an appropriate transportation provider.

Call Process Flow

Figure 2:
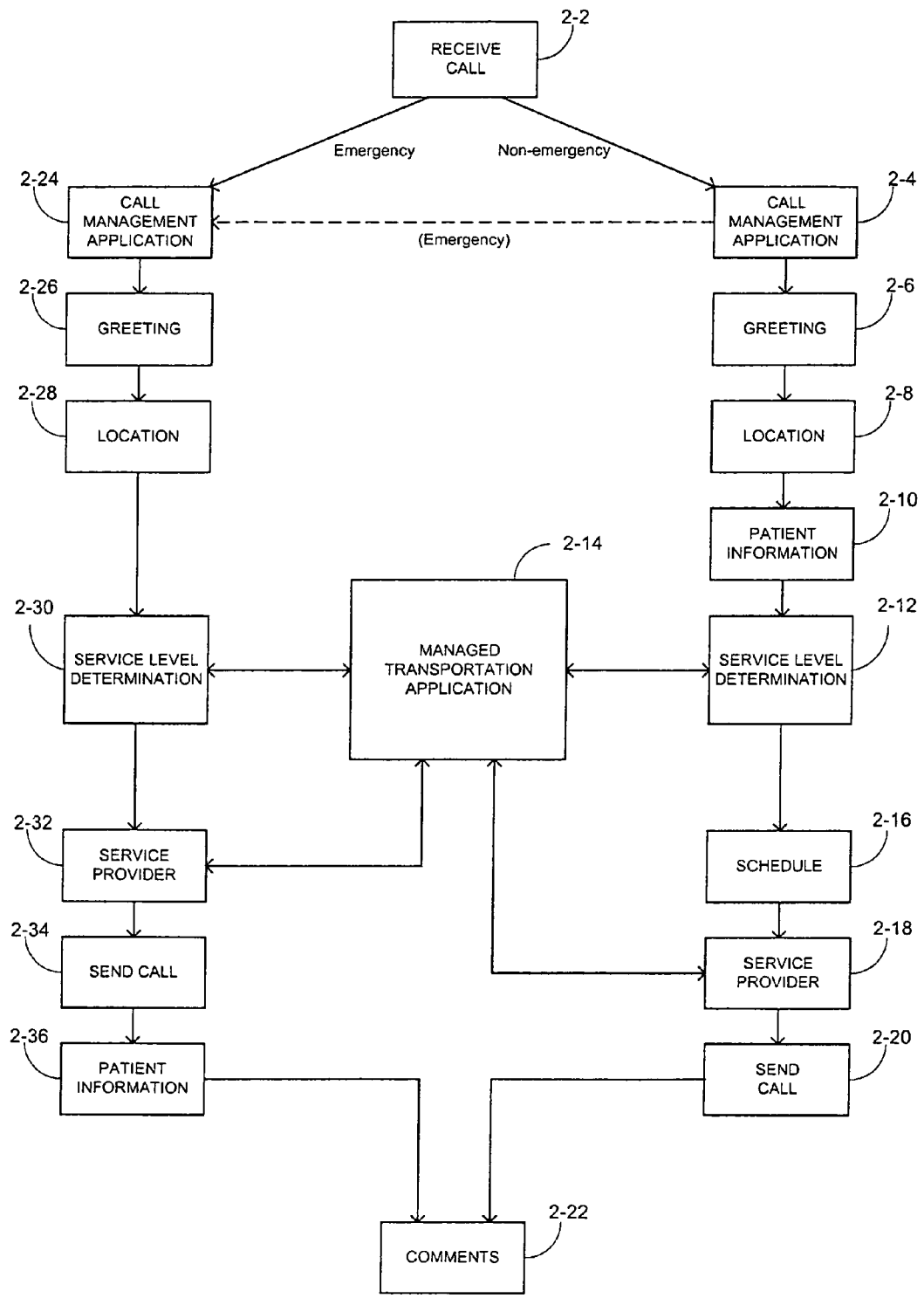
FIG. 2 illustrates a basic call handling process flow in accordance with the preferred embodiment.

FIG. 2 illustrates default call process flows in the managed transportation system of the preferred embodiment for emergency and non-emergency calls.

When a call is received 2-2, it is first determined whether the call is an emergency call or a non-emergency call. In the preferred embodiment, this determination is made based on the access number used by the caller to contact the call center. Calls received through access numbers provided to health plan members (i.e. patients) are presumed to be emergency calls and are therefore routed directly to a call center agent. Calls received through other access numbers, such as those provided to physicians or hospitals, are presumed to be non-emergency calls. In the preferred embodiment, an agent may reclassify a call as an emergency call or a non-emergency call when appropriate.

If a call is a non-emergency call, a call management application 2-4 is invoked and the caller is presented with an automated greeting and prompted to enter preliminary information such as a patient's health plan member ID number and a facility code indicating a facility from which the patient is to be transported. The caller is also enabled to indicate whether the call is an emergency call. If the call is indicated to be an emergency, then an emergency call process flow is used as described below.

Where the caller does not indicate that the call is an emergency call, the call is passed from the call management application 2-4 to an agent and a greeting module 2-6 is invoked. The greeting module 2-6 presents a user interface to the agent that displays the information entered by the caller using the call management application 2-4 and displays an appropriate greeting for the agent to read to the caller. The greeting module enables the agent to enter the name of the caller, a call back number of the caller, and caller type (e.g. doctor, nurse, discharge planner, or patient). The greeting module also determines, or allows the call center agent to specify, the contract and any subcontract governing the request for transportation.

A location module 2-8 is then invoked. The location module 2-8 presents a user interface that enables the agent to enter information concerning the location from which the patient is to be transported, referred to hereinafter as the response location, and the location to which the patient is to be transported. The location module also provides searching capabilities for assisting the call center agent to locate information such as address information for a location.

A patient information module 2-10 is then invoked. The patient information module 2-10 user interface enables the agent to view and verify patient information such as name, age, address and member ID. The patient information module 2-10 also enables the agent to search for patients by name and to view patient related insurance information and contract specific data. At this stage of the call the agent enters the name of the attending or sending physician. The agent may also enter the patient's name, member ID, date of birth, and social security number, if these were not already determined by the system based on the caller's earlier input to the call management application.

The patient information module 2-10 also displays a determination of the patient's eligibility for transportation that is made by the system. The eligibility determination is typically based on the member type of the patient, the facility type of the response location, and contractual obligations between the patient's healthcare provider and the facility, and is made using information provided by the patient's insurer.

A service level determination module 2-12 is then invoked. The service level determination module 2-12 user interface includes tools for determining the service level and response time required for the requested transportation. The service level determination module utilizes a managed transportation application 2-14, which presents a series of questions requesting information from the caller that is used to determine a level of service that is appropriate in accordance with a protocol based on the diagnosis and other factors such as equipment or medications required during transport. The managed transportation application 2-14 typically prompts the agent to ask specific questions of the caller to obtain the information needed to determine a service level and response time. In the preferred embodiment, different protocols for determining service level may be employed depending on factors such as the location of the caller (e.g. at home or at a facility such as a hospital), and the different protocols may be provided using different applications, as described in more detail below. In some instances an alternative protocol may be used to determine service level and other parameters based on alternative information such as the patient's major complaint.

After a level of service has been determined, a schedule module 2-16 is invoked. The schedule module 2-16 enables the agent to view and edit transportation schedule information for the patient such as times and locations.

After scheduling is complete, a service provider module 2-18 is invoked. The service provider module 2-18 enables the agent to determine an appropriate transportation provider for the requested transportation. The service provider module 2-18 provides a list of transportation providers. The list includes transportation providers that are identified based on the geographic location of the transport request, and transportation providers identified through the application of business rules representing contractual obligations between health insurance providers and transportation providers, the latter of which are determined by the managed transportation application 2-14. The combined list is presented to the agent in a color coded format that indicates the basis upon which each listed provider is recommended, and from which the agent is enabled to select a particular transportation provider to provide the scheduled transport.

After a transportation provider has been selected, a send call module 2-20 is invoked. The send call module 2-20 enables the agent to dispatch the request for transportation to the selected transportation provider and to record confirmation of acceptance by the transportation provider.

After the request for transportation has been sent, a comments module 2-22 is invoked. The comments module 2-22 enables the agent to note any information about the call that was not already captured by the other modules. The agent is also enabled to manually invoke the comments module 2-22 at any time during the call process.

As noted above, different default call process flows occur for emergency and non-emergency calls. When a call is determined to be an emergency call based on the access number dialed by the caller, the call management application 2-24 requests only a member ID number, and the call is then passed to an agent. The greeting module 2-26 is invoked, followed by the location module 2-28 and then the service level determination module 2-30. After determining a level of service in a manner similar to the non-emergency case, the service provider module 2-32 is invoked, followed by the send call module 2-34. By presenting the modules in this order in the case of an emergency call, the system obtains the minimum information necessary to dispatch the request for transportation without requesting additional information (e.g. patient information) that is not strictly necessary for that purpose. Once the request has been dispatched using the send call module 2-34, the patient information module 2-36 is invoked, enabling the agent to obtain patient information if possible. Finally the comments module 2-22 is invoked.

Managed Transportation System Architecture

Figure 3:
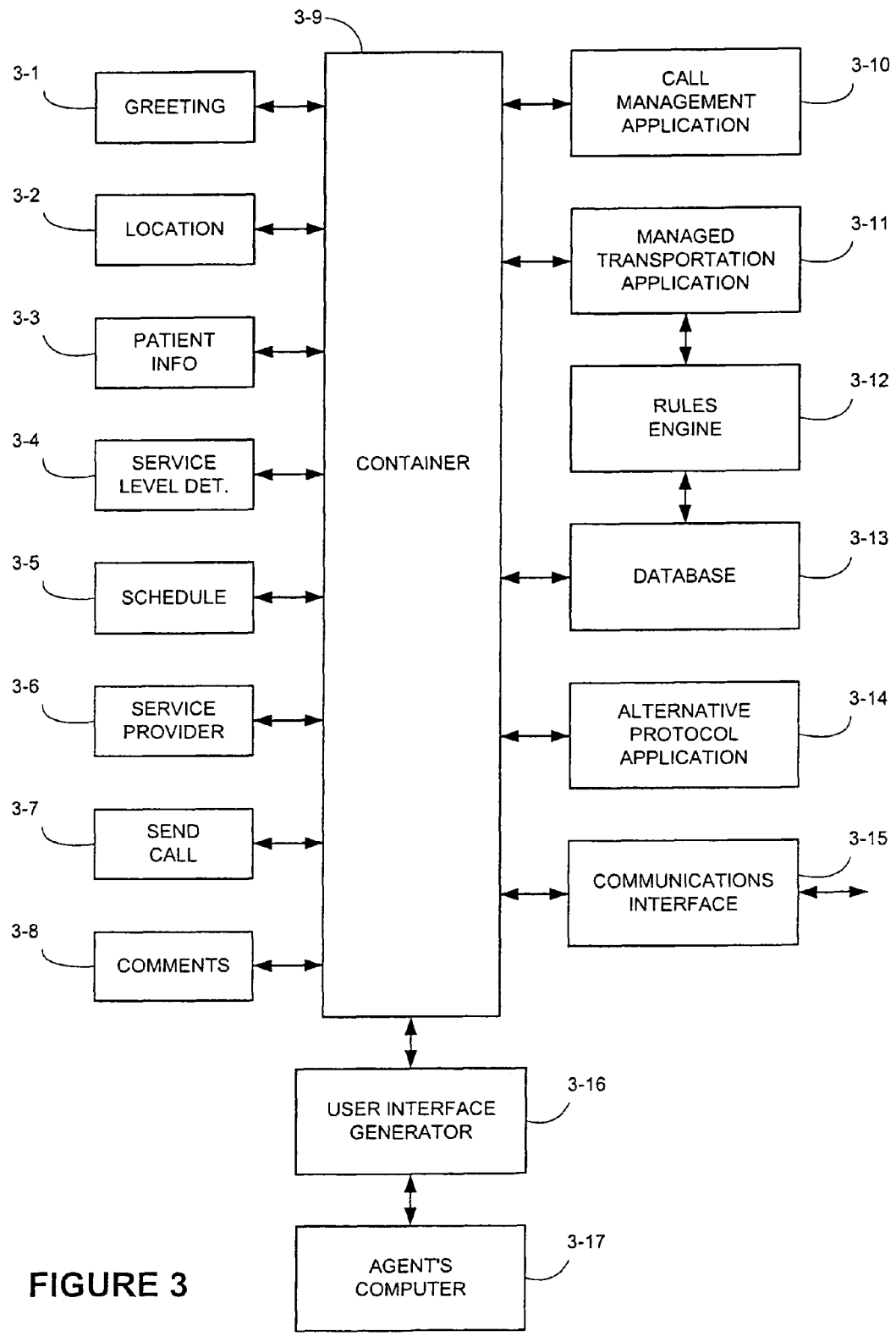
FIG. 3 is a view of a call management server architecture in accordance with a preferred embodiment of the invention.

FIG. 3 shows a generalized schematic view of the architecture of a preferred embodiment of the call management server of FIG. 1. In general the server comprises a set of modules 3-1 through 3-8 whose actions are coordinated by a container application 3-9. The container 3-9 also serves as an interface between the modules 3-1 through 3-8 and other system elements 3-10 through 3-15. The container 3-9 is also interfaced with call center agent computers 3-17 through a user interface generator 3-16 that generates user interfaces for and receives input on behalf of the various system modules.

The modules 3-1 through 3-8 provide various user interfaces and tools that are displayed to and used by call center agents. The modules include a greeting module 3-1, location module 3-2, patient information module 3-3, service level determination module 3-4, schedule module 3-5, service provider module 3-6, send call module 3-7, and comments module 3-8, as described previously with respect to the call process flow diagram of FIG. 2. The user interface module 3-16 generates a basic user interface that is displayed by call center agent computers 3-17 as thin clients, and within which user interfaces of the modules 3-1 through 3-8 are displayed.

The server further includes a call management application 3-10. In the preferred embodiment, this element is implemented using the APROPOS call management application produced by Apropos Technologies. The call management application 3-10 generates an Integrated Voice Response (IVR) greeting that is presented to the caller and that requests the caller to enter information using the telephone keypad. In the preferred embodiment, the call center uses a variety of access numbers that are selectively provided to individuals based on the individual's status as a health plan member (patients and their families), medical facility staff (e.g. doctors and nurses), or external provider staff (e.g. clinic or nursing home staff), and based further on additional factors such as the calling location. Accordingly, the greeting and questions presented to the caller by the IVR are tailored to the particular type of caller and calling location based on the access number that is used by the caller to contact the call center.

The call management application 3-10 obtains initial information for the call from the caller. The modules 3-1 through 3-8 are then utilized to obtain further information in an interactive process between the caller and the call center agent. As the call management application 3-10 and then each module 3-1 through 3-8 is utilized, a call record is built for the call. The call record is stored in the database 3-13 and contains all information acquired from the caller as well as all additional information determined by the system for that call.

The patient information module 3-3, the service level determination module 3-4 and the service provider module 3-6, communicate with a managed transportation application (MTA) 3-11. The MTA 3-11 works in conjunction with a rules engine 3-12 to perform five basic tasks: determination of an appropriate level of service, response time and response interval; determination of an original transaction classification for a transportation request (i.e. a determination of responsibility for the cost of transportation); determination of the caller's authority to change a service level or response time previously determined by the MTA; determination of a final transaction classification where the service level or response time was changed; and, determination of appropriate service providers for the requested transportation.

The rules engine 3-12 contains hard-coded (hereinafter "special") rules that are applied in making each of the aforementioned determinations. The rules engine 3-12 also applies dynamic rules stored as rules tables in a database 3-13. The rules engine of the preferred embodiment is implemented using the Aion Inference Engine application produced by Computer Associates.

The rules of the rules engine 3-12 are of two basic types. The first type of rules are service level determination rules. Service level determination rules represent the various governmental regulations applicable at the location at which the requested transportation is to occur, and that mandate the minimum level of service required (such as critical care or advanced life support) based on various factors such as the patient's diagnosis or major complaint, the patient's equipment needs, and the patient's medication needs. The second type of rules of the rules engine are business rules. Business rules represent the contractual provisions the govern the requested transportation. Such provisions may operate between the patient and the patient's insurer, the patient's insurer and a transportation provider, the patient's insurer and the call center operator, the call center operator and a transportation provider, the patient's insurer and a facility to or from which the patient is to be transported, and so forth. These rules are used to determine contractual features of the requested transportation such as a response time and response interval, responsibility for the cost of transportation, authority to change the service level of transportation, and any required transportation provider.

The system further includes an alternative protocol application 3-14 that applies an alternative protocol for determining a service level. In the preferred embodiment, the ProQA application produced by Priority Dispatch Corporation is used as an alternative protocol for calls originating from a patient's home. The ProQA application is used in this manner in the preferred embodiment because its determinations are based on assessments of symptoms as they would typically be expressed by a lay person, whereas the MTA protocol bases determinations on diagnoses, equipment and medicine needs as they would be expressed by a medical professional such as a physician or nurse. When the alternative protocol application 3-14 is employed, a code generated by the alternative protocol application representing a patient's major complaint is translated into a service level using a translation table, and that service level is then used by the system in further processing.

The managed transportation system also includes a communications interface 3-15. The communications interface 3-15 provides communication links to entities such as transportation service providers through various means including facsimile, CAD (computer assisted dispatch), internet, and remote print.

Basic User Interface

Figure 4:
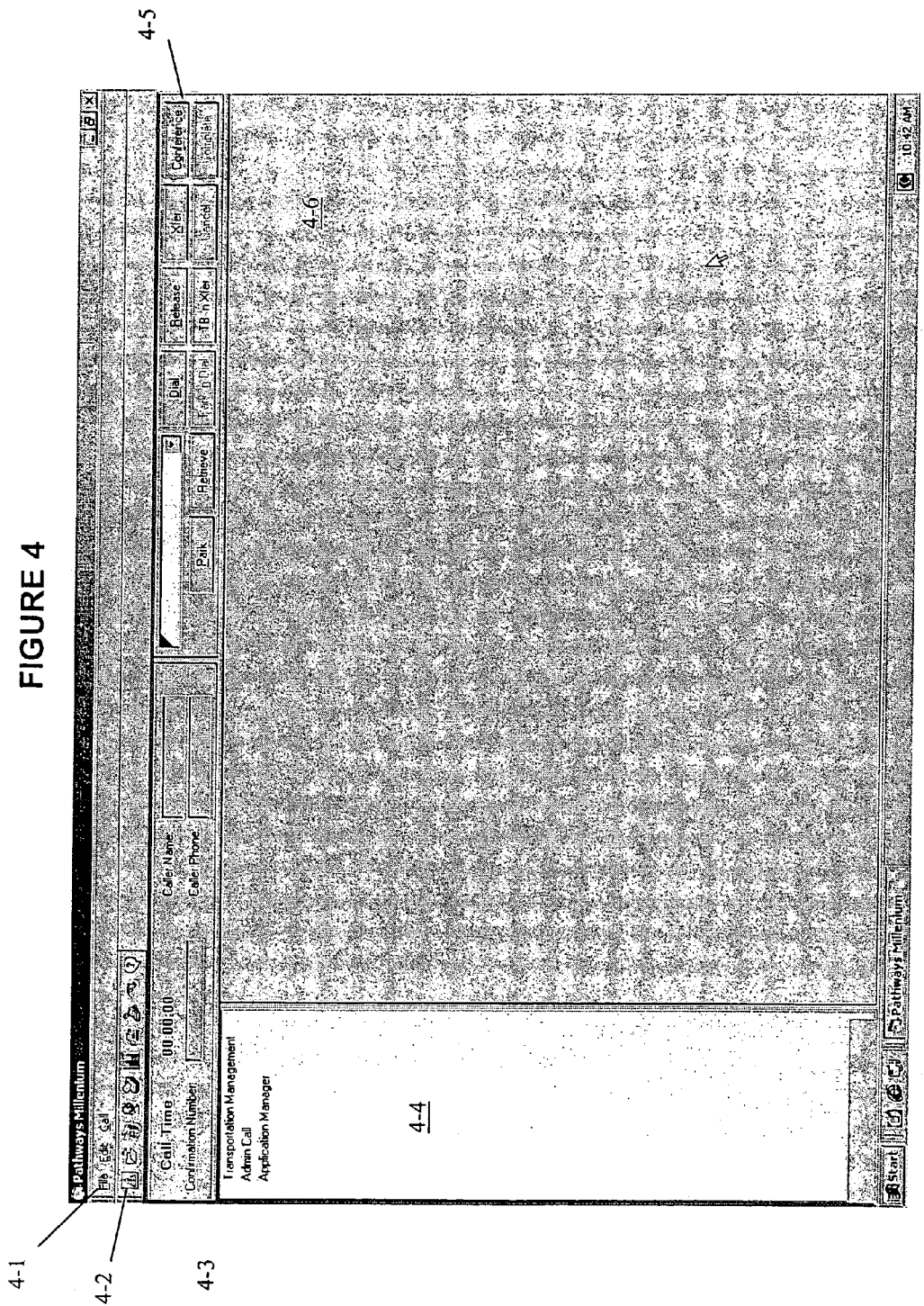
FIG. 4 is a view of a graphical user interface presented by a container application of the preferred embodiment.

FIG. 4 shows the basic user interface displayed to call center agents in accordance with the preferred embodiment. The basic user interface is comprised of a menu bar 4-1, a toolbar 4-2, a call information display 4-3, a module control window 4-4, a computer telephony interface (CTI) 4-5, and a module interface display window 4-6 in which the user interfaces of system modules are displayed.

The menu bar 4-1 includes File, Edit, and Call menus. The File menu provides an exit command that terminates the agent's use of the application. If the exit command is invoked during a call, a message "call is in progress" is displayed and the agent is asked to indicate whether the call should be cancelled or put on hold. The Edit menu provides commands for editing information displayed in the user interface. The Call menu includes open, hold and cancel functions that are replicated in the toolbar 4-2 as discussed below.

The toolbar 4-2 includes buttons that invoke functions including Start Call, Open, Hold/Retrieve Hold, Cancel, Messaging, Address Verification, Card File, and Help buttons. The Start Call function is used to start a call manually. The Open function enables an agent to query information regarding calls previously received. When the Open button is clicked, a Call Look-Up module is displayed, enabling an agent to search for calls based on various criteria including the date of the call, call status, agent handling the call, response or destination of requested transportation, queue type, last name or first name of the patient, call confirmation number, or call reference number. The Hold/Retrieve Hold function puts a call on hold in a local queue (for the current agent) or a global queue (for any of a pool of agents). The Cancel function is used to cancel a call at any stage in the call taking process. The Messaging function is used to share messages between other system users. The Address Verification function allows the agent to verify the existence of an address. The Card File function enables an agent to store and look up phone numbers and addresses. The Help button function invokes help topics.

The call information display 4-3 displays a variety of call and call timing information including the elapsed call time, a call confirmation number, and the caller's name and telephone number.

The module control window 4-4 lists the modules available for call processing in the default order in which they will be presented for the current call.

The basic user interface also includes a CTI (Computer Telephony Interface) 4-5 that enables the agent to utilize various telephone system functions. The CTI has four modes of operation: (1) Normal, (2) Take Back and Transfer (TBT), (3) Transfer/Conference, and (4) Park. In the Normal mode, all of the buttons on the CTI panel are enabled, and an agent may initiate a telephone call by entering a number into the number field and then operating a Dial Button. The TBT mode allows an agent to take back and transfer a call. If a phone number displayed in the phone number field of the CTI has an asterisk as the first character, the TBT function is enabled. An agent can click on the TBT button to enable the take back and transfer or may simply dial the phone number with the asterisk. The Transfer/Conference mode is the default mode for the CTI once a phone number is dialed. The call can be transferred or connected to a conference in this mode. The Park mode is used to put a call on hold. An agent can click the Park or Park and Dial button to put an existing call on hold. Clicking on the Park Retrieve button allows an agent to retrieve a call and place the call mode back to Normal.

Greeting Module

Figure 5:
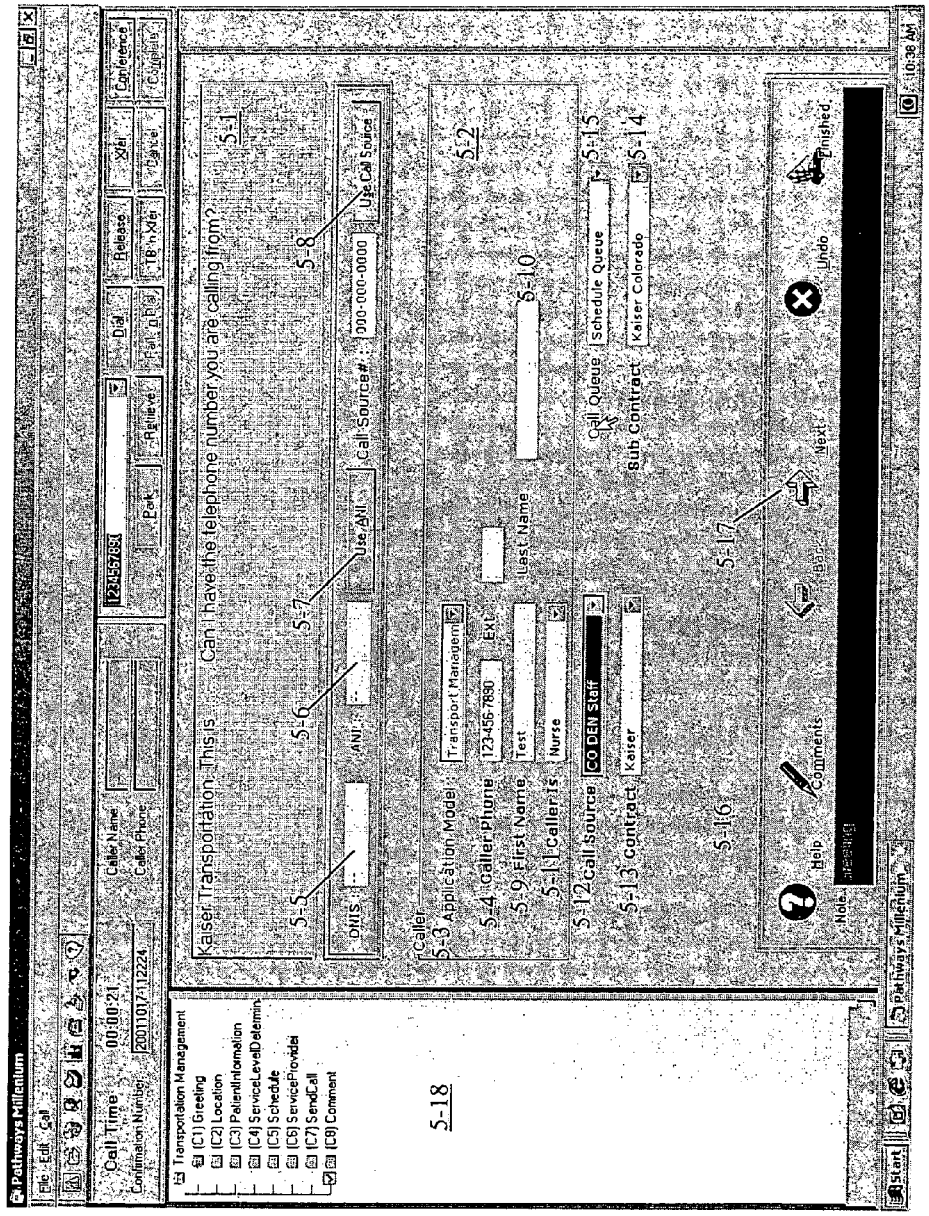
FIG. 5 is a view of a graphical user interface displayed by a greeting module of the preferred embodiment.

FIG. 5 shows the user interface generated for the greeting module in accordance with the preferred embodiment. The greeting module presents a greeting that may be read to a caller by an agent, and displays information about the caller to the agent.

The greeting module user interface includes a greeting field 5-1 that displays a greeting to be read by the agent to a caller. The greeting presented for a particular call is automatically tailored to that call based on a number of factors including the called number, the Member ID, and facility code, the latter two of which are captured by the call management application in the case of a non-emergency call. In the illustrated example, the tailored greeting enables the agent to greet the caller in the name of the caller's health insurance provider.

The greeting module user interface further includes a caller box 5-2 that contains fields for entering information concerning the caller. The caller box further includes a caller's call back telephone number field 5-4. The agent may enter a call back number obtained from the caller in the call back number field. The number dialed by the caller to access the call center is shown in a DNIS box 5-5. The agent may also use a number obtained by automatic number identification (ANI), shown in an ANI field 5-6, by operating a use ANI button 5-7. The agent may alternatively enter the call source number (the access number dialed by the caller) by operating a use call source button 5-8.

The greeting module user interface further includes first name 5-9 and last name 5-10 fields. These fields may be automatically populated through reference to records stored in the database based on information previously captured by the call management application such as member ID and facility code, or may be filled in by the agent.

The greeting module user interface also includes a 'Caller Is' field 5-11 comprising a drop down list tool that allows the agent to select a type of caller from the list. The list may be automatically populated with types of callers based on the access number used by the caller to contact the call center. The various caller types typically include patient, health plan staff, social worker, nurse, physician, and the like. The agent is also enabled to fill in a caller type manually. This information may be used in later processing, for example to determine authority to upgrade the service level of the requested transportation.

The greeting module user interface further includes call source 5-12, contract 5-13 and subcontract 5-14 fields. The call source field 5-12 may be populated through reference to database records based on the access number used by the caller. The contract 5-13 and subcontract 5-14 fields indicate the contracts and subcontracts of the operator of the managed transportation system that govern the disposition of the call. The values in these fields are used in later processing as triggers for the business rules that are applicable in making other determinations in regard to the requested transportation. These fields may be populated through reference to database records based on previously captured information such as the access number used by the caller. If the contract and subcontract are not known from the access number, the contract 5-13 and subcontract 5-14 fields are provided with drop-down lists that enable the agent to select the appropriate contract and subcontract. These features may be used, for example, where the access number used by the caller is not determinative of the contract and subcontract. For example, a call received through an access number provided to a hospital may not be indicative of the particular contract or sub-contract at issue since the hospital may provide services in conjunction with several insurance providers that each have transportation contracts with the managed transportation system operator.

The greeting module user interface further includes a call queue field 5-15. The call queue field 5-15 indicates whether a present caller has indicated that the call is an emergency or a non-emergency call.

The greeting module user interface also includes a comments button 5-16 that enables the agent to invoke the comments module to record any additional greeting-related information. It will be seen from further description that a comments button is provided for each module of the system. Comments entered in conjunction with a given module are stored in a module-specific format.

The greeting module user interface also includes a Next button 5-17 that invokes the next module in the default sequence of the call. A next button 5-17 is provided for each module of the system. Operation of the next button 5-17 in this module or in any module causes all data captured by that module to be stored to a call record in the database. When the agent operates the next button 5-17 of the greeting module, a background search of database records is initiated to locate any previously stored information that is associated with the information obtained for that call by the call management system and the greeting module, such as the member ID, and the patient name if the caller is a patient.

The greeting module user interface illustrated in FIG. 5 also shows the contents of the module control window 5-18 that are displayed when a module is invoked, in this instance the greeting module. The module control window 5-18 includes text listing each module that will be invoked during the call in the order in which they will be invoked. An open folder icon next to a module name indicates that it is currently invoked, while a closed folder indicates that the module is not currently invoked. A check mark next to a module name indicates that all required fields of the module have been populated. The control window 5-18 enables the agent to invoke any module by clicking on that module in the control window.

Location Module

Figure 6:
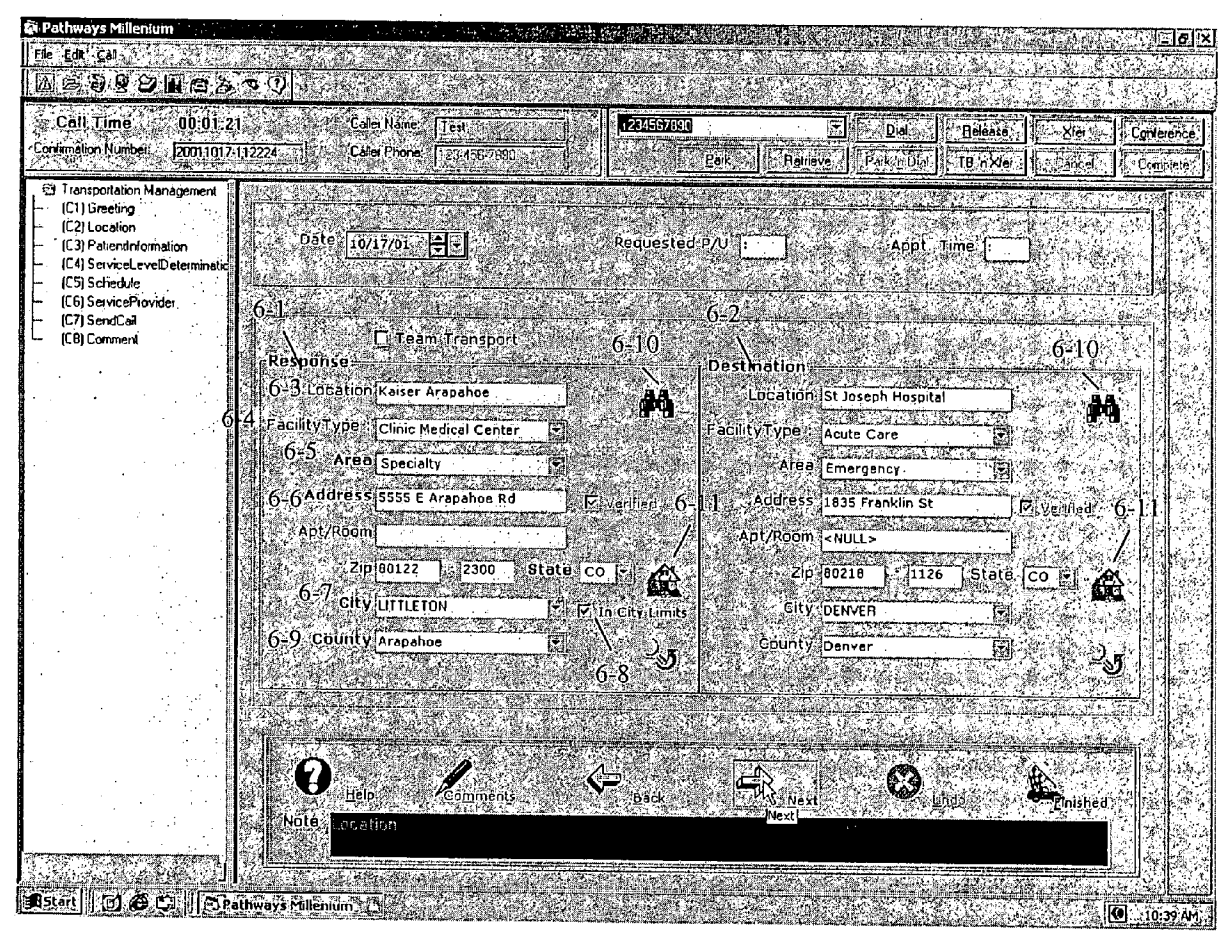

FIG. 6 shows the user interface presented to the agent for the location module of the preferred embodiment. The location module enables the agent to specify the response location where the patient will be picked up and a destination location to which the patient will be transported.

The location module user interface includes a response box 6-1 that presents fields for information concerning the location from which transport will originate, and a destination box 6-2 that presents fields for information concerning the destination of the transport. The response box 6-1 includes fields that display a location 6-3, the facility type 6-4 of the response location, a specific area 6-5 for pickup within the facility, the facility address 6-6, and the city 6-7 and county 6-9 of the facility.

The fields of the response box 6-1 are automatically populated, to the extent possible, based upon information captured by the call management system and by previously invoked modules. For example, a facility ID obtained by the call management system may be used to retrieve associated location information from a database to populate the fields of the response box.

The area field 6-5 specifies a particular area within the facility at the pickup location. For example, typical areas at a hospital facility are an emergency room or an ICU. The area field 6-5 includes a drop-down list tool that is populated with a list of areas based on previously stored information concerning the facility. If no information about a facility is stored, then all possible area names are included in the area list.

The response box 6-1 further includes a check box 6-8 for indicating whether the response location is within the city limits of the listed city. This information is used later in the call process when searching for a transportation provider, as described further below. A team transport box 6-12 may be checked to indicate that the transportation requires picking up or dropping off a member of a medical team such as a nurse or a doctor, which may require the transportation vehicle to make a stop at an additional location and to spend more time providing the transport as a result.

The destination box 6-2 has fields similar to those of the response box 6-1. The destination box 6-2 fields are typically populated manually by the agent using information provided by the caller.

Figure 7B:
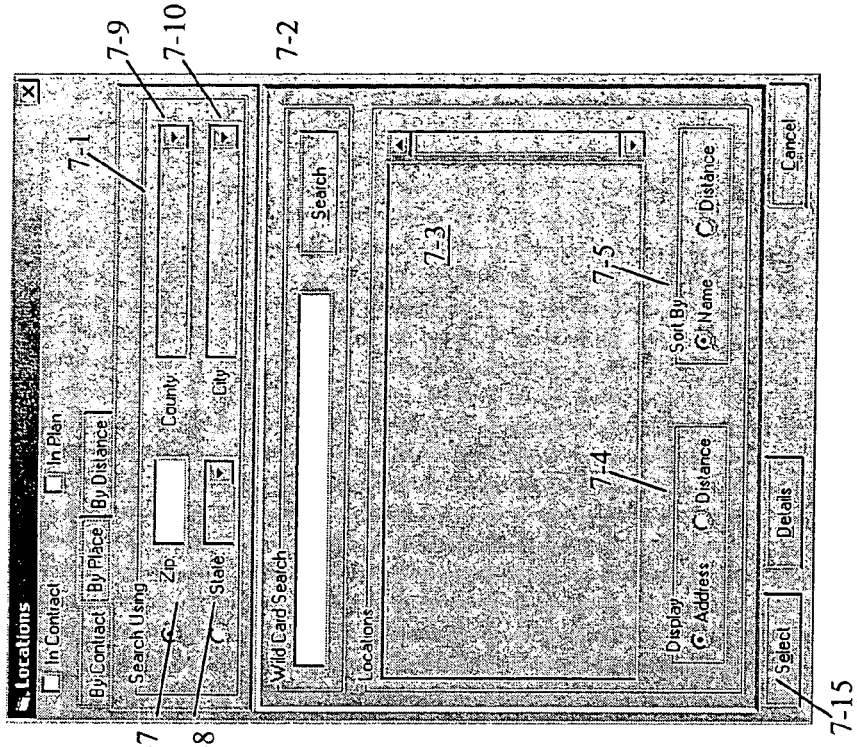
FIGS. 7a, 7b and 7c are views of graphical user interfaces displayed by a location search tool of the location module of the preferred embodiment.
Figure 7A:
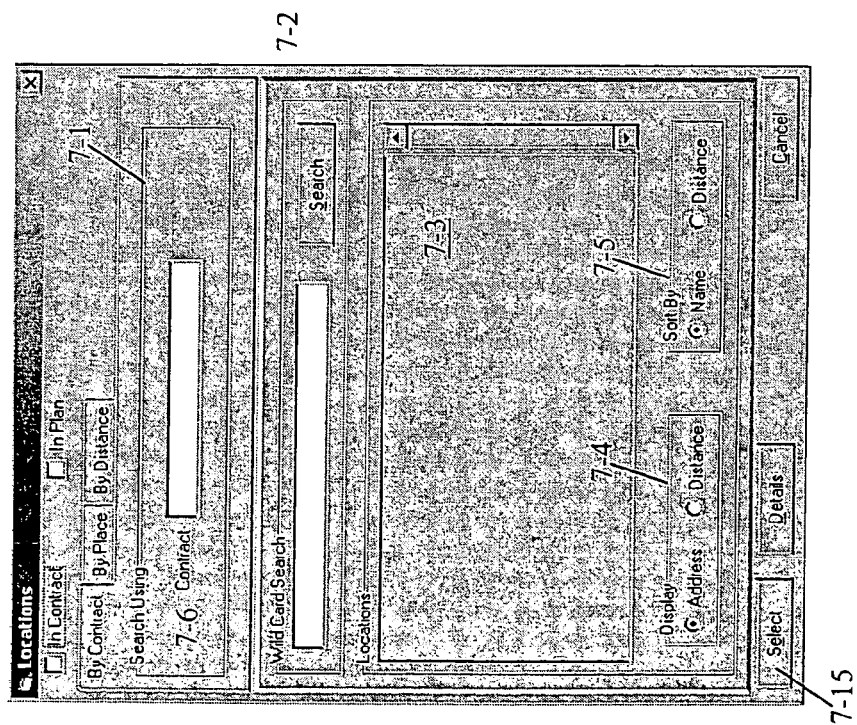
Figure 7C:
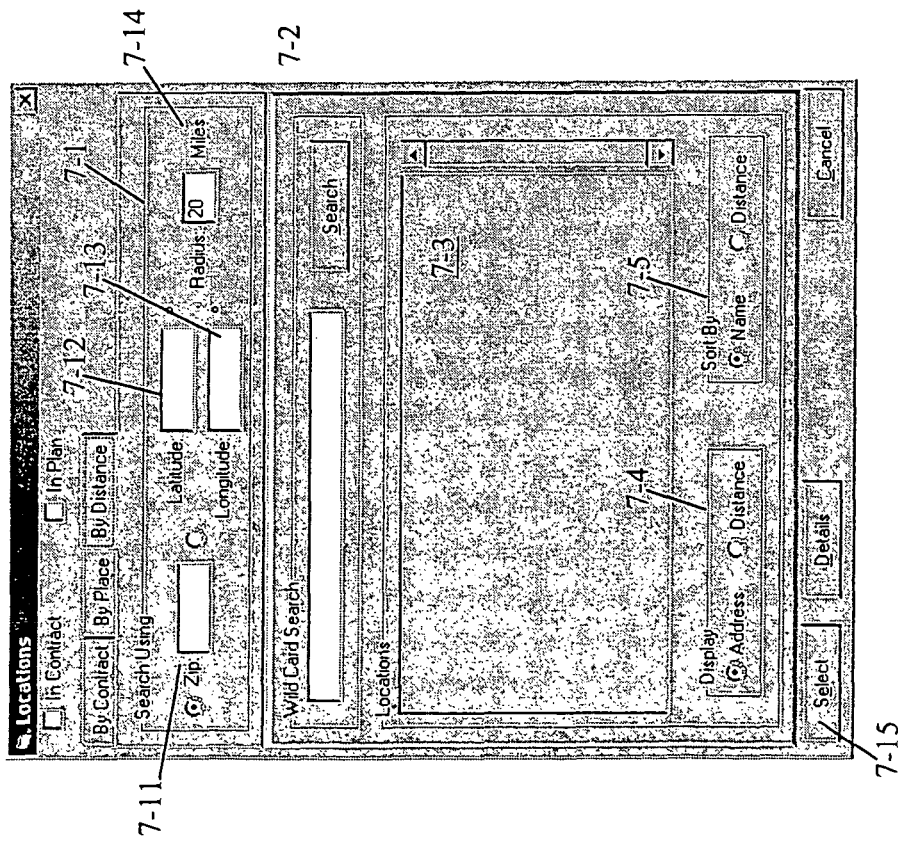

The response box 6-1 and destination box 6-2 further include location search buttons 6-10 that invoke a location search function, and address search buttons 6-11 that invoke an address search function. FIGS. 7a-7c show search forms provided by a location search module invoked by the location search button 6-10. The search by contract form of FIG. 7a allows the agent to search for a response location by contract. The search form includes a search box 7-1, a wildcard search box 7-2, a search results display box 7-3, and a display tool 7-4 and sort tool 7-5 that control the manner in which the search results are displayed. "In contract" and "in plan" check boxes are provided to limit search results to locations that are designated in a contract between the call center operator and the patient's insurer, and that are designated in the patient's insurance plan, respectively. In the search by contract search form, the search box includes a contract field 7-6 in which the agent may enter a contract identifier. In the search by place form of FIG. 7b, the agent is enabled to enter search parameters in a zip code field 7-7, a state field 7-8, a county field 7-9, and a city field 7-10. In the search by distance form of FIG. 7c, the agent is enabled to enter search parameters in a zip code field 7-11, latitude and longitude fields 7-12 and 7-13, and a radius field 7-14. If the location search module is invoked from the destination location panel, then the location search module opens to the distance search form, allowing the agent to search for a facility that is within a given distance (e.g. 25 miles) from a desired response location.

Each of the search forms further includes a select button 7-15 that enables the agent to select particular search results to populate the response or destination location fields of the location module user interface.

Patient Information Module

Figure 8:
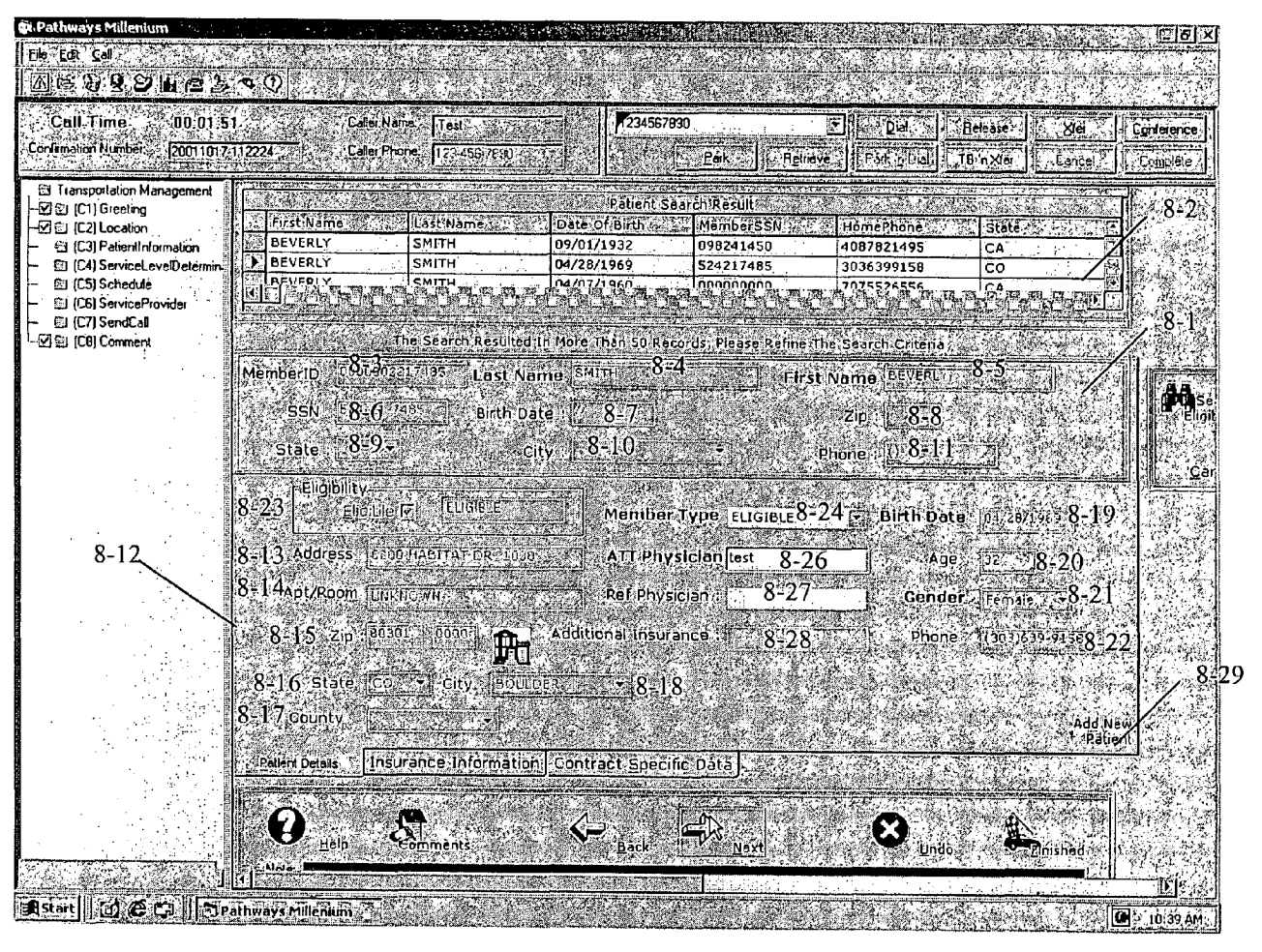

FIG. 8 shows the user interface presented to the agent for the patient information module in accordance with the preferred embodiment. The patient information module assists the agent to capture detailed information concerning the patient to be transported and displays that information to the agent.

The fields of the patient information module are populated, to the extent possible, using information captured earlier in the call, such as a member ID number, and any additional information that may be determined from the previously captured information, such as a patient name and address associated with the member ID number, and patient eligibility. The remaining fields of the patient information module user interface are filled in by the agent.

The patient information module user interface includes a search criteria box 8-1 and a search result box 8-2. The search criteria box 8-1 includes fields that enable the agent to enter search parameters to search for patient information, such as a patient's member ID 8-3, last name 8-4, first name 8-5, social security number 8-6, date of birth 8-7, zip code 8-8, state 8-9, city 8-10, telephone number 8-11, or a combination of those parameters. At least one of the member ID, social security number and last name must be specified in order to perform a search. Search results are displayed in the search results box 8-2 in the form of a list that can be sorted by fields.

When a search result is selected from the search results list, the corresponding patient information is populated in fields of a patient information box 8-12 that includes fields for displaying patient information. These fields include address-related fields such as street address 8-13, apartment number 8-14, zip code 8-15, state 8-16, county 8-17, and city 8-18. Other patient-related information fields include date of birth 8-19, age 8-20, gender 8-21 and telephone number 8-22.

The selection of a patient from the search results list also invokes an eligibility determination using the patient information and other information captured during the course of the call. The eligibility determination is made using an eligibility file provided by the patient's insurer. The eligibility information typically includes the patient name, membership number, line of business (e.g. commercial, Medicare, Medicaid), effective date of coverage and term date. The result of the eligibility determination is indicated in an eligibility box 8-23, which indicates the patient's eligibility status in an eligibility field. Eligibility is also indicated in a member type field 8-24. The member type field includes a variety of member types including eligible, commercial, Medicare, not eligible, patient pay, part A/expanded care, hospice, veterans administration, and SPN member identification. Where eligibility is unknown, the agent may enter the patient's eligibility status. This may be used, for example, where a patient has entered an incorrect member ID number, or where the patient's call was not initially handled by the call management application and so no member id was provided. The call center agent may also override a determination of ineligibility based on absence of a record for the patient in the eligibility file. This may be necessary, for example, where the patient is known to be eligible by a physician making the request for transportation, but the patient's eligibility information is not yet included in the eligibility file.

The patient information module user interface also includes fields for entry of treatment-related information by the agent, including the attending physician 8-26, the referring physician 8-27, and information concerning additional insurance 8-28.

The patient information module also enables the agent to add a new patient and transportation conditions for the patient to the system if the patient in question is not already in the system. The agent may invoke this process by operating an add new patient button 8-29. This creates a new patient record using the patient information captured in the fields of the patient information module. Initially, the eligibility box will be unchecked so the agent can select the appropriate eligibility criteria for the new patient. While this feature allows a new patient to be entered, the patient's eligibility status cannot be permanently established in this manner, since that information must come from the patient's insurer. Therefore eligibility for a newly entered patient must be determined on a case by case basis.

The aforementioned user interface features are presented on a patient details form. In addition, the patient information module also presents an insurance information form and a contract specific data form that allows viewing and entry of insurance information for the patient and contract specific data relating to any contract between the call center operator and the patient's insurer.

Service Level Determination Module

Figure 9:
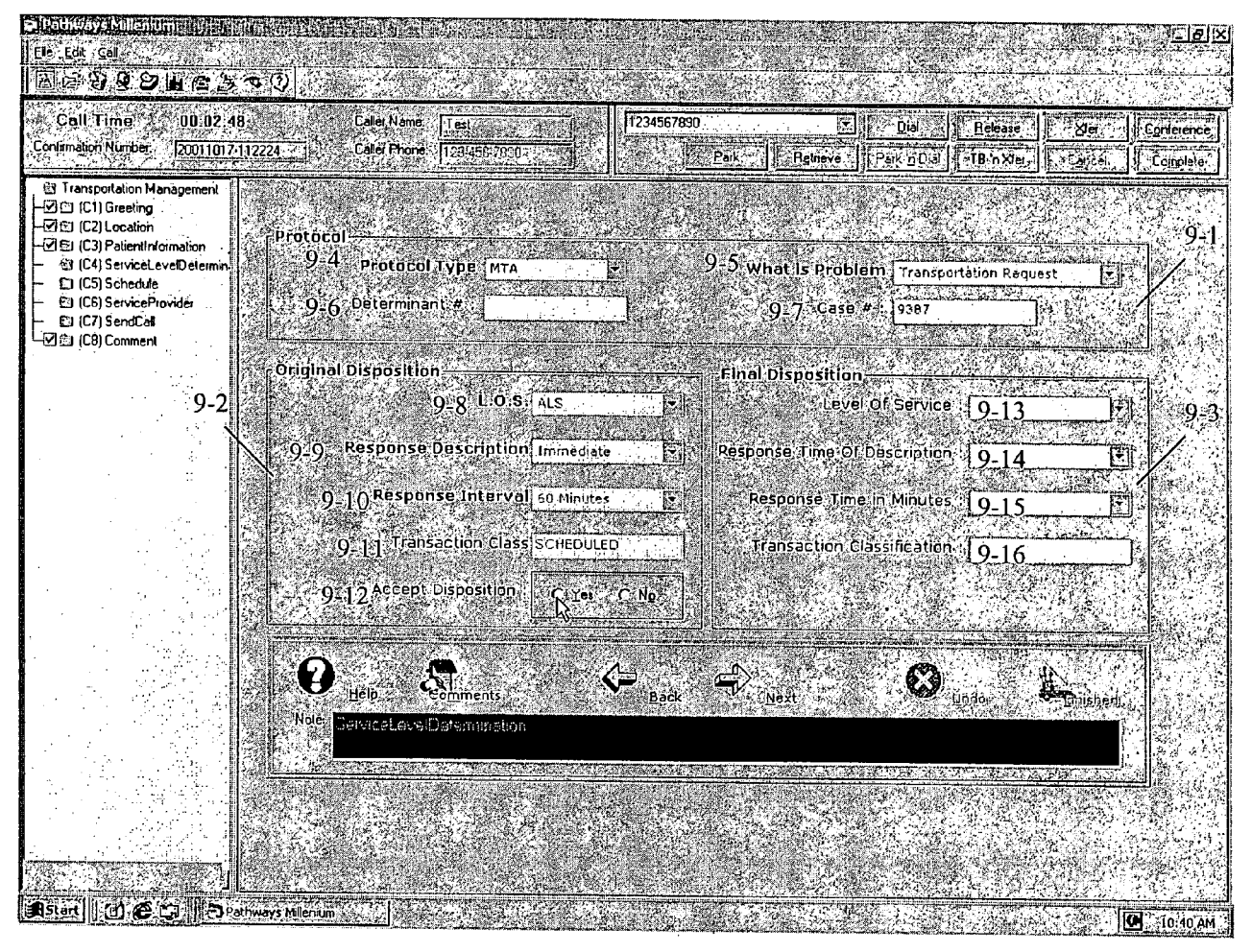

FIG. 9 shows the user interface presented for the service level determination module of the preferred embodiment. The service level determination module determines the particular type of transportation service that is required by a given patient, as well as performance related criteria such as a response time and response interval, and a determination of responsibility for the cost of transportation.

The user interface of the service level determination module includes a protocol box 9-1. The protocol box includes a protocol type field 9-4, problem field 9-5, determinant number field 9-6, and case number field 9-7. The protocol type field 9-4 indicates a type of protocol that will be employed in making a service level determination for the call. Different protocols may be employed for determining the service level depending on factors such as contractual requirements, whether the call is emergency or non-emergency, the location of the patient (e.g. at a facility or at home), and whether the transportation has been pre-authorized. In the preferred embodiment the ProQA protocol, which makes decisions based on symptoms as they would be expressed by a lay person, is used for calls originating from a patient's home or where required by a contract governing the disposition of the call, whereas a protocol implemented in the MTA based on diagnosis, equipment and medication information is used for other calls. The protocol type to be used for a given call may be determined automatically based on information captured earlier in the call, such as the access number used by the caller, or may be set manually by the call center agent.

The user interface further includes an original disposition box 9-2 and a final disposition box 9-3. The original disposition box includes a level of service field 9-8, response time description field 9-9, response interval field 9-10, transaction classification field 9-11, and an accept disposition box 9-12.

The service level represents the type of transportation equipment and personnel needed for the transportation, and is generally dictated by governmental regulations. In the preferred embodiment, the following levels of service are used: critical care transport (CCT), advanced life support (ALS), basic life support (BLS), wheelchair (WC), or transport not authorized (TNA). In the MTA protocol of the preferred embodiment, the service level determination is made using service level rules and additional special rules that utilize information concerning the patient's diagnosis or diagnoses, the patient's equipment needs, the patient's medication needs, and the facility types and areas of the response location and destination. While some of this information is captured at earlier stages of the call, other information must be acquired at this stage of the call in order to make these determinations.

The response time and response interval are contractually defined performance standards imposed on the transportation provider by patient's insurer for the particular type of transportation required. The response time represents an acceptable amount of time required to provide the transportation, and the response interval represents an amount by which the response time may vary depending on circumstances such as geographic location. The response times used in the preferred embodiment include: 911, Urgent, Immediate, Scheduled, Pre-Scheduled, or Repatriation. Response time and response interval are determined through the application of business rules representing the contract provisions applicable to the requested transportation.

The transaction classification is a contractually defined classification of the transportation that indicates responsibility for the cost of transportation, which includes in some instances the manner in which that cost is assessed. The transaction classification is determined in accordance with business rules representing the relevant contractual provisions.

Figures 10A, 10B:
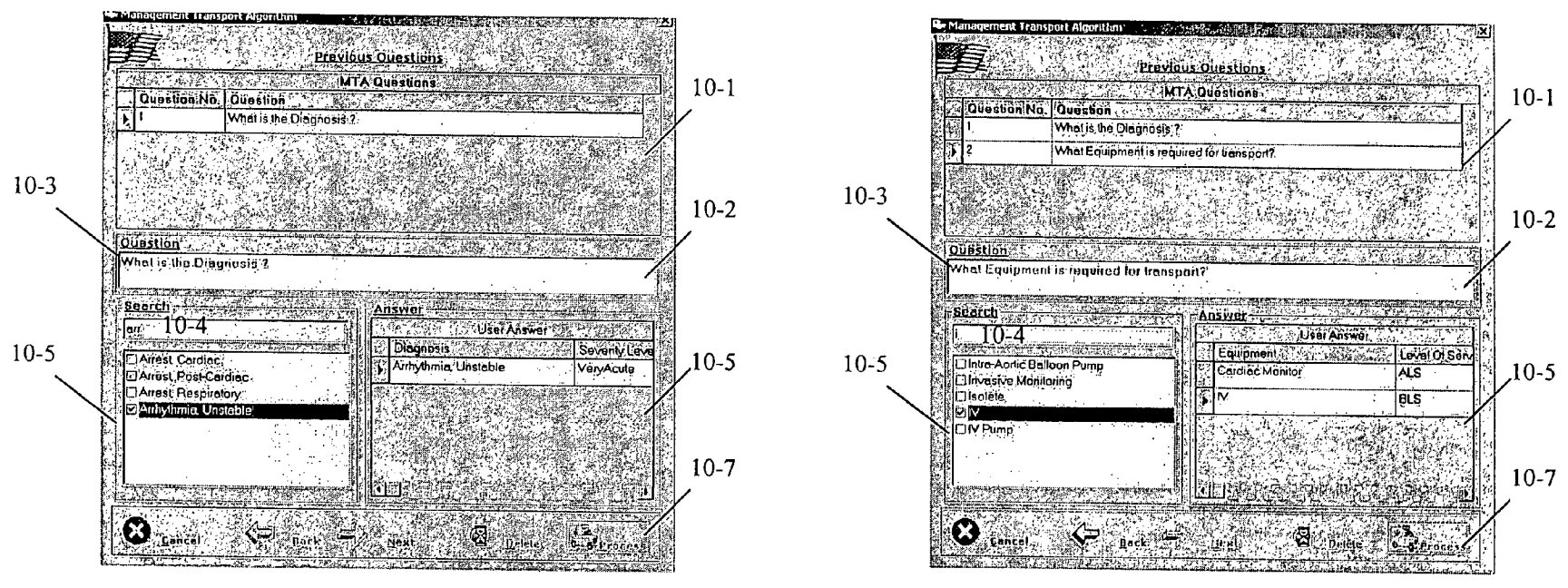

The service level determination in accordance with the MTA protocol may require consideration of many items of information relating to the patient's diagnosis, equipment needs and medication needs, and therefore the service level determination process of the preferred embodiment uses a series of specialized user interfaces that are presented in an iterative manner to elicit all information necessary to make a service level determination. FIG. 10a shows a first user interface generated for purposes of service level determination using the MTA protocol. The user interface includes a question list box 10-1 that displays a list of all questions that have been asked during the course of the service level determination process, and a question box 10-2 that displays the present question being asked. A search box 10-3 includes a field 10-4 for entering a diagnosis term to be searched, and a search results list 10-5 shows all search results. When a character string is entered in the search box 10-3 of this user interface, a search for diagnoses containing that character string is performed using an MTA diagnosis rules table. A box next to each search result may be checked to enter the selected search result into a field of an answer box 10-6, indicating that the entered term is responsive to the present question. In the case of diagnosis information, up to four diagnoses may be entered. Once responses have been selected, the agent may operate a process button 10-7 that submits the information to the MTA for further processing.

As shown in FIG. 10b, after processing the current call information including the diagnosis information provided in response to the preceding question, the MTA returns an additional question regarding the equipment needed for transport. The user interface presented to the agent for this question is similar to the user interface presented to the agent for diagnosis determination as shown in FIG. 10a. When a character string is entered in the search box 10-3 of this user interface, a search for equipment names containing that character string is performed using an MTA equipment rules table.

Figure 10D:
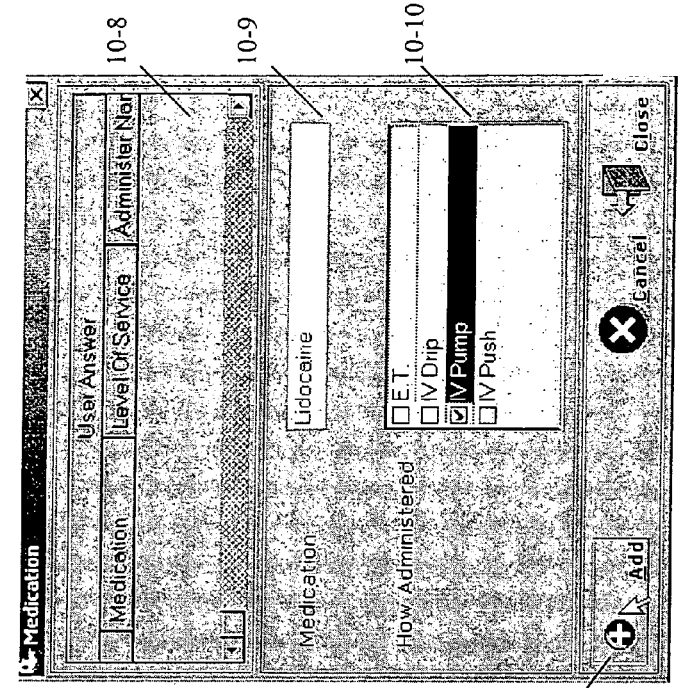
Figure 10C:
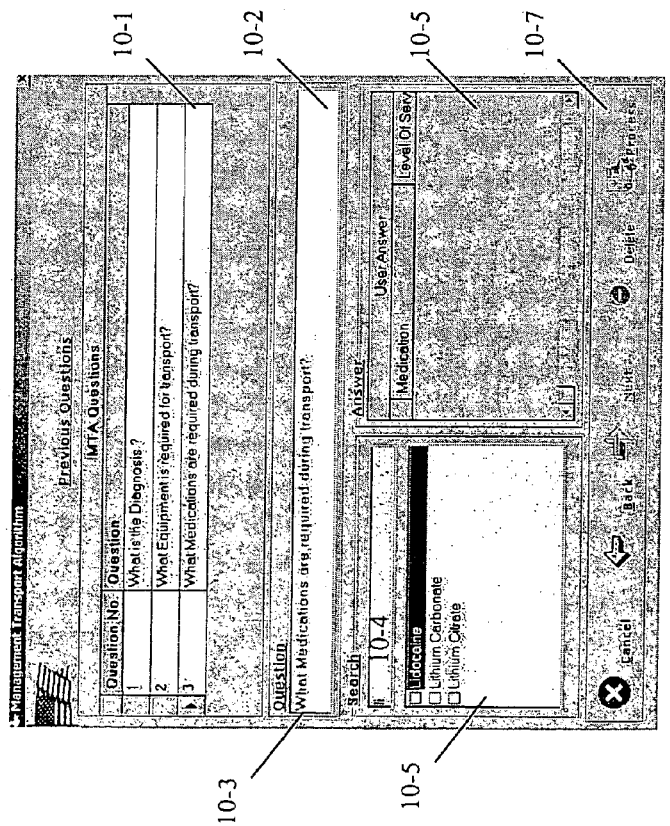

As shown in FIG. 10c, after processing the current call information including the diagnosis and equipment information provided in response to the preceding questions, the MTA returns an additional question regarding the medications required by the patient. The user interface presented to the agent for this question is similar to the user interfaces presented to the agent for diagnosis and equipment determination as shown in FIGS. 10a and 10b. When a character string is entered in the search box 10-3 of this user interface, a search for medication names containing that character string is performed using an MTA medication rules table.

The selection of a particular medication may require further information concerning the manner of administration of the medication. FIG. 10d shows the user interface presented to the agent for questions concerning administration of medication. This user interface includes a medication list 10-8. Since only one medication was selected in the previous user interface, the list is blank in this instance. The user interface further includes a medication field 10-9 that displays a selected medication from the medication list 10-8, or the single medication at issue where the list is not populated. The user interface further includes an equipment field 10-9 that displays methods of administration of the currently selected medication. A box next to each method of administration may be checked to indicate that the method of administration is applicable to the patient. An add button 10-11 submits the information to the MTA.

Figure 10E:
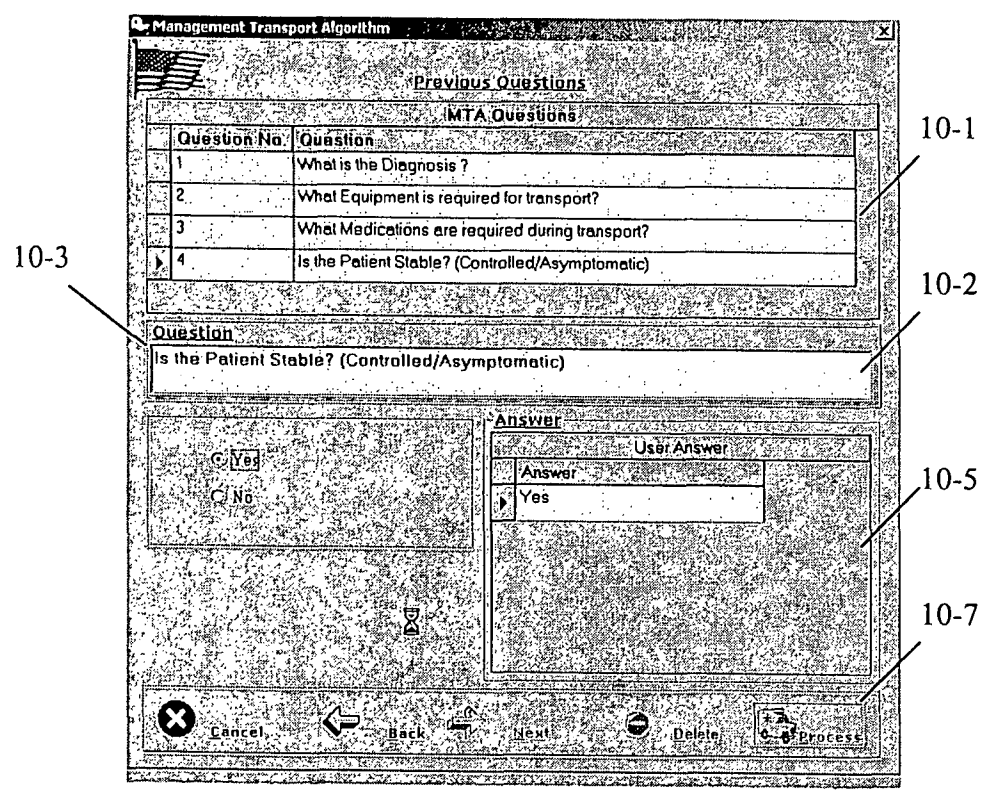

As shown in FIG. 10e, after processing the aforementioned information, the MTA returns an additional question regarding the patient's stability. The user interface presented to the agent for this question is similar to the user interfaces presented to the agent for diagnosis, equipment and medication determination as shown in FIGS. 10a, 10b and 10c.

Although the aforementioned sequence of questions is representative of a typical call using the MTA protocol, in some instances not all of the information obtained in that sequence is required in order to determine service level and other parameters of the requested transportation. This is discussed further below in regard to the operation of the MTA.

The information submitted to the MTA using the interfaces shown in FIGS. 10a-10e is processed by the MTA along with other information captured during the call to generate determinations of a service level, response time, and response interval. These determinations are used to populate the fields 9-8 through 9-10 of the original disposition box 9-2 of the service level determination module user interface of FIG. 9.

The MTA also determines a transaction classification for the requested transportation. The transaction classification represents a determination of responsibility for payment of the cost of the requested transportation and is made using business rules that encode the contractual obligations among the patient, the patient's insurer, and in some instances, the call center operator and the chosen transportation service provider. For example, a contract between the patient and the patient's insurer may provide that the insurer will cover the expenses of transportation in emergency situations and in situations where non-emergency transportation is requested by a physician. Another contract between the insurer and the transportation provider may stipulate that emergency transportation is fully billable at cost on a per event basis to the insurer, whereas non-emergency transportation is billable to the insurer under a capitated (i.e. fixed fee for all transportation within a given period of time) cost structure. It should be understood that a variety of other contractual arrangements involving other factors may be devised, and that a variety of other factors may be relevant to determining liability for the cost of transportation.

The result of the transaction classification determination is used to populate the transaction classification field 9-12. Transaction classifications used in the preferred embodiment include: scheduled, non-scheduled, 911, patient pay, leakage, upgrades/overrides, and hospice, each of which represents a different apportionment of liability for transportation costs.

The original disposition box 9-2 also includes an accept disposition box 9-12 that enables the agent to indicate whether the caller accepts the service level and response time determined by the MTA as the original disposition. If the caller accepts the original disposition, the fields 9-13 through 9-16 of the final disposition box are populated using the information contained in the fields 9-8 through 9-11 of the original disposition box. In some instances the caller may not agree with the original disposition and may request a change in the disposition, such as a change in service level or response time. For example, a physician requesting transportation for a patient may request an increase in the level of service to a level that is higher than the level determined using the applicable protocol. Similarly, the caller may for example request a more rapid response time than is provide for by the business rules used to determine response time. In the event that the caller does not accept the original disposition, the parameters of the desired final disposition are entered in the fields 9-13 through 9-15, and the MTA processes that information to determine whether the desired final disposition is authorized, and to determine a transaction classification for the final disposition. This determination is made through the application of business rules that represent the contractual provisions governing the authority of various parties to alter the original disposition, and the changes in liability for cost of transportation that result based on various factors such as the party making the request and the nature of the changes requested.

Schedule Module

Figure 11:
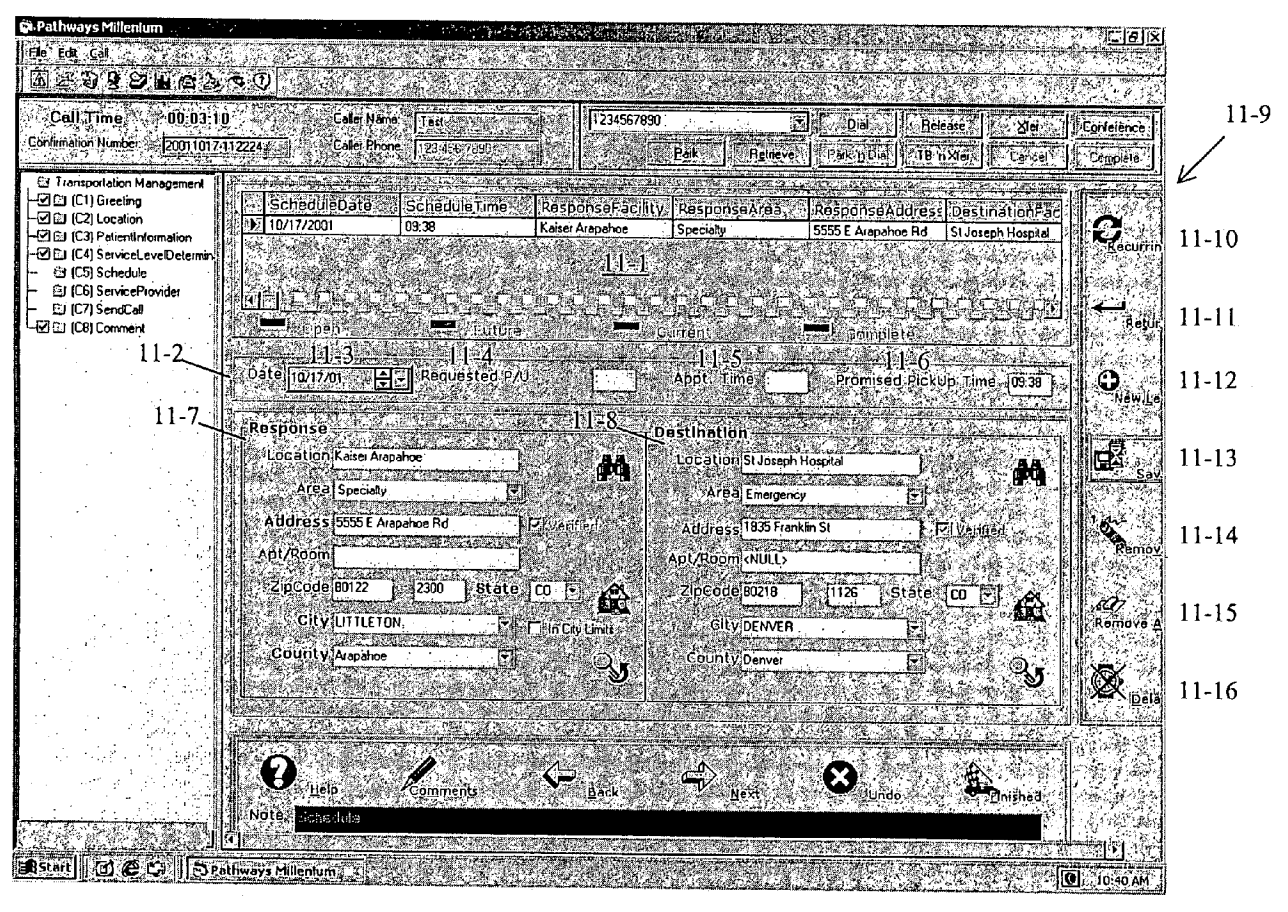

FIG. 11 shows the user interface presented for the schedule module in accordance with the preferred embodiment. The schedule module enables the agent to specify the dates and times of the transportation required by the patient.

The user interface includes a schedule box 11-1 that shows a schedule of transportation that has been arranged for the patient. In the preferred embodiment the schedule is color coded to indicate the status of each entry in the schedule.

Time parameters for transportation to be scheduled may be entered using tools and fields provided in a time box 11-2. The time box 11-2 includes a date tool 11-3, a requested pick-up time field 11-4, an appointment time field 11-5, and a promised pick-up time field 11-6.

The user interface further includes a response location box 11-7 and a destination location box 11-8. These boxes contain fields and search tools for information concerning the response location and destination location of the transport to be scheduled. Most of the fields in these boxes are the same as fields included in the response location and destination location boxes 6-1 and 6-2 of the location module user interface illustrated in FIG. 6, and in the case of a one way transport these fields are populated with the same values as in the location module user interface.

The schedule module user interface further includes a tool bar 11-9 providing tools that enable the agent to create and edit the schedule. A save tool 11-13 enables the agent to save a newly created transport to the transportation schedule in the transportation schedule box 11-1. A remove tool 11-14 enables the agent to remove a scheduled transport from the transportation schedule. A remove all tool 11-15 enables the agent to completely clear the transportation schedule. A delay tool 11-16 invokes a delay form that enables the agent to enter information explaining reasons for any delay in transportation.

Figures 12A, 12B, 12C:
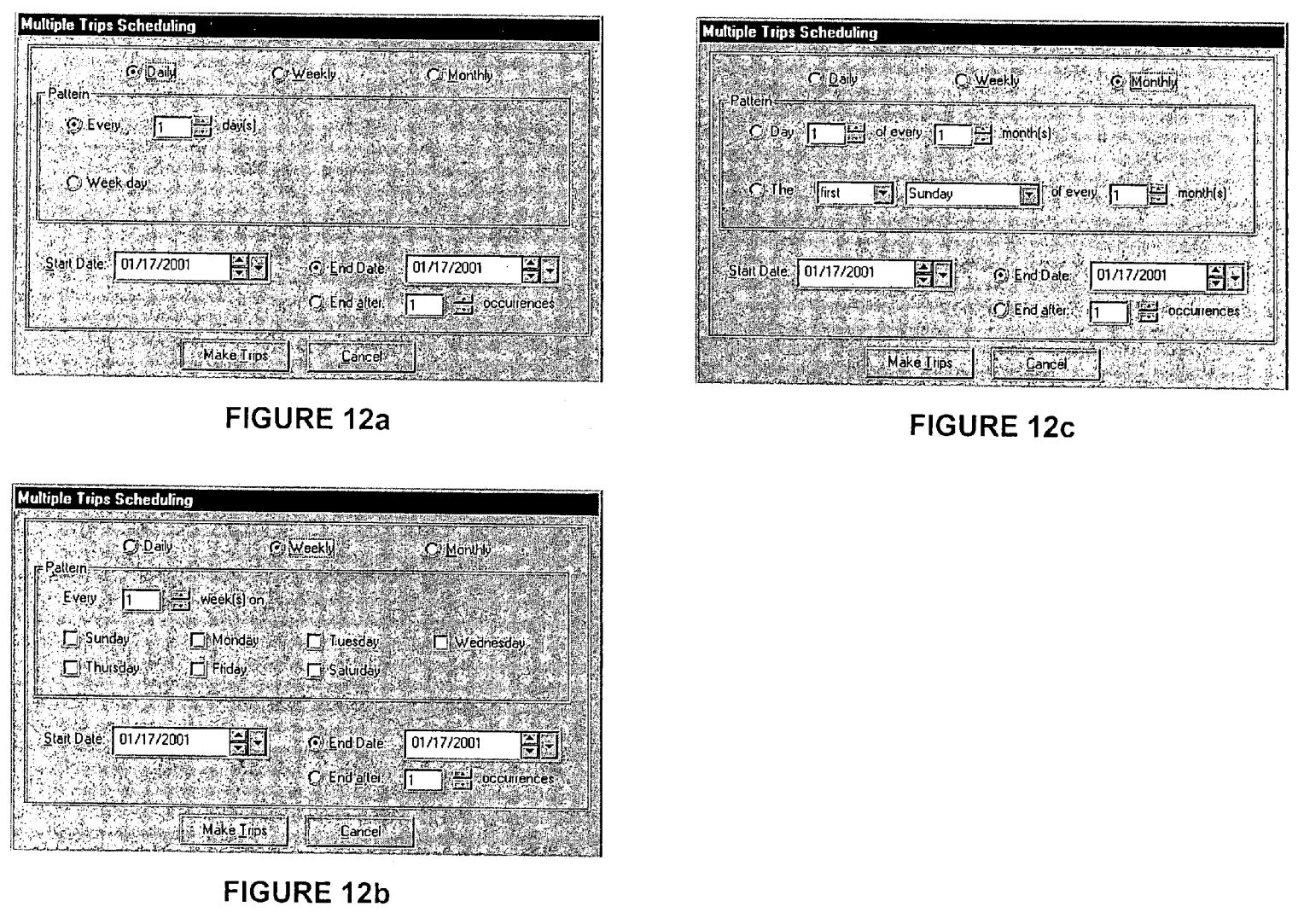

The tool bar 11-9 also includes a recurring transport tool 11-10 that enables the agent to create a schedule for a transport that will recur multiple times. FIGS. 12a-12c show various instances of a user interface invoked by operation of the recurring transport tool 11-10. This user interface provides tools that enable the agent to specify the time and data parameters of the recurring transport. FIG. 12a shows the tools that are provided to configure a daily trip, FIG. 12b shows the tools that are provided to configure a weekly trip, and FIG. 12c shows the tools that are provided to configure a monthly trip.

The tool bar 11-9 further includes a return trip tool 11-11. This tool adds a return leg to a previously scheduled transport, automatically using the destination of the selected transport as the origin of the return leg, and the origin of the selected trip as the destination.

The tool bar 11-9 also includes a new leg tool 11-12, which enables the agent to adds a new leg to a previously scheduled transport, automatically using the destination of the selected transport as the origin of the new leg, and leaving open the destination information of the new leg for the agent to fill in.

Service Provider Module

Figure 13:
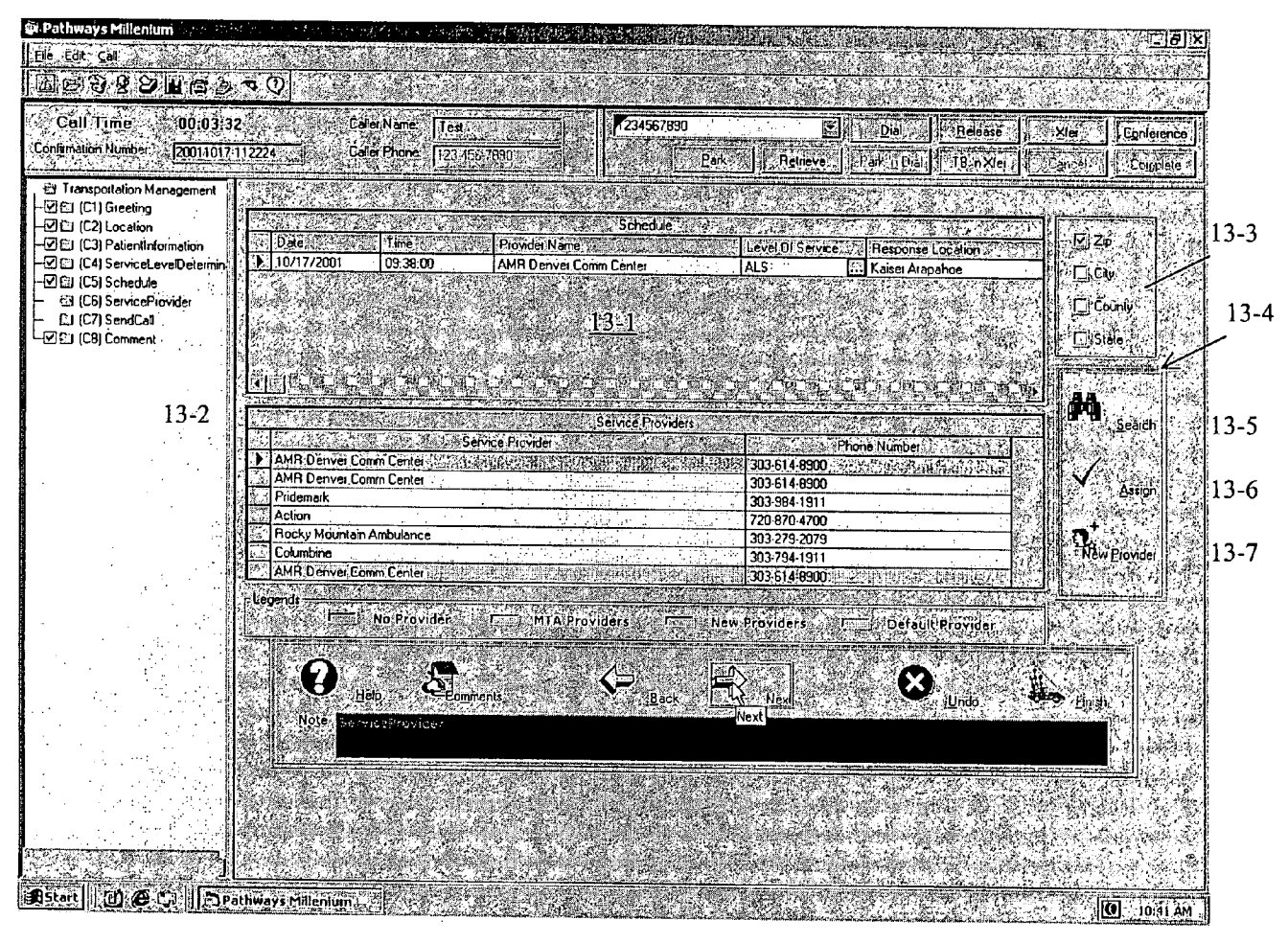

FIG. 13 shows the user interface presented for the service provider module in accordance with the preferred embodiment. The service provider module enables an agent to select an entity to provide the scheduled transportation.

The service provider module user interface includes a schedule box 13-1 that shows the transportation scheduled for the patient. The user interface further includes a service provider box 13-2 that displays a list of available transportation providers. In the preferred embodiment, the list of transportation providers is the product of two separate provider searches that are executed by the system and combined. The first search is a simple geographic search based on the locations of the response and destination. The second search is performed by the MTA and takes into account a variety of factors in addition to geography, including disposition, service level, and any contract and subcontract obligations of the managed transportation system operator or a health insurance provider, such as a requirement that all transport of a particular service level in a particular region to be paid for by a particular insurance provider is to be dispatched to a particular transportation provider.

The user interface further includes a tool bar 13-4 that includes buttons for invoking a search tool 13-5, an assign tool 13-6, and a new provider tool 13-7. The search tool 13-5 enables the agent to invoke a manual search for transportation providers. The basis of the search may be selected by the agent by checking a search option in a search box 13-3 located above the toolbar 13-4. The assign tool 13-6 assigns a selected transportation provider to a leg of the requested transportation schedule. The new provider tool 13-7 enables the agent to add a new provider to the database. Providers added in this manner are valid only for the current call.

In the preferred embodiment, the search results are displayed in the transportation provider box 13-2 in a color coded format that indicates the criteria underlying the inclusion of each transportation provider in the list. The agent is enabled to select from among the transportation providers in the list. In the case of a return, recurring, or multi-leg trip, the transportation provider selected for the first leg is automatically duplicated for the additional or remaining legs, but may be changed by the agent.

Send Call Module

Figure 14:
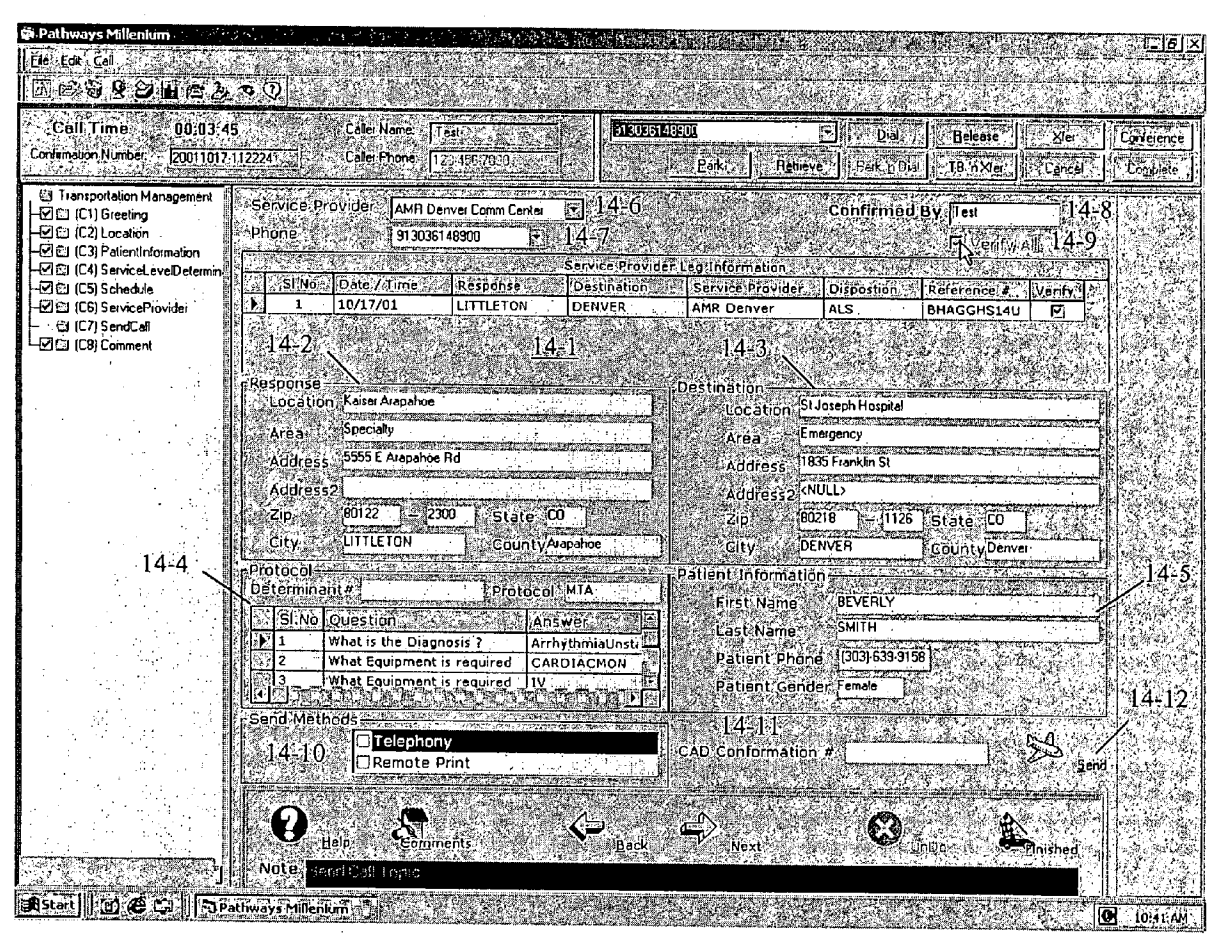

FIG. 14 shows the user interface presented for the send call module in accordance with the preferred embodiment. The send call module is used to send a request for transportation to a selected service provider.

The send call module user interface includes boxes displaying information to be provided to the service provider. These include a schedule box 14-1 that displays the basic schedule of the transportation to be requested, a response box 14-2 that displays information describing the response location, a destination box 14-3 that displays information describing the destination location, a protocol box 14-4 that displays information concerning the transportation protocol such as the patient's diagnosis and the equipment and medications required for the transport, and a patient information box 14-5 that displays information about the patient such as the patient's name, gender and telephone number.

The send call module user interface further includes fields relating to the transportation service provider to whom the request is to be dispatched. A service provider field 14-6 displays the selected service provider, and includes a drop down list tool that enables selection of another service provider. A phone number field 14-7 displays the telephone number of the selected service provider. A confirmed by field 14-8 is used to capture the name of the transportation provider agent who accepted the request for transportation. A verify all box 14-9 is also provided. This box is checked by the call center agent when acceptance of the transportation request by the transportation provider is verbally confirmed, and in response the system generates a final confirmation number.

The send call module user interface further includes a send methods box 14-10 that provides options that may be checked to select a method by which the request for transportation is to be sent. The displayed options are customized to the selected transportation service provider. For example, requests may be sent by telephone, remote print, or computer aided dispatch (CAD). In the case of CAD, a CAD confirmation number is displayed in a CAD confirmation number field 14-11 when received. The agent may initiate the sending of the request using a send button 14-12.

Comments Module

Figure 15:
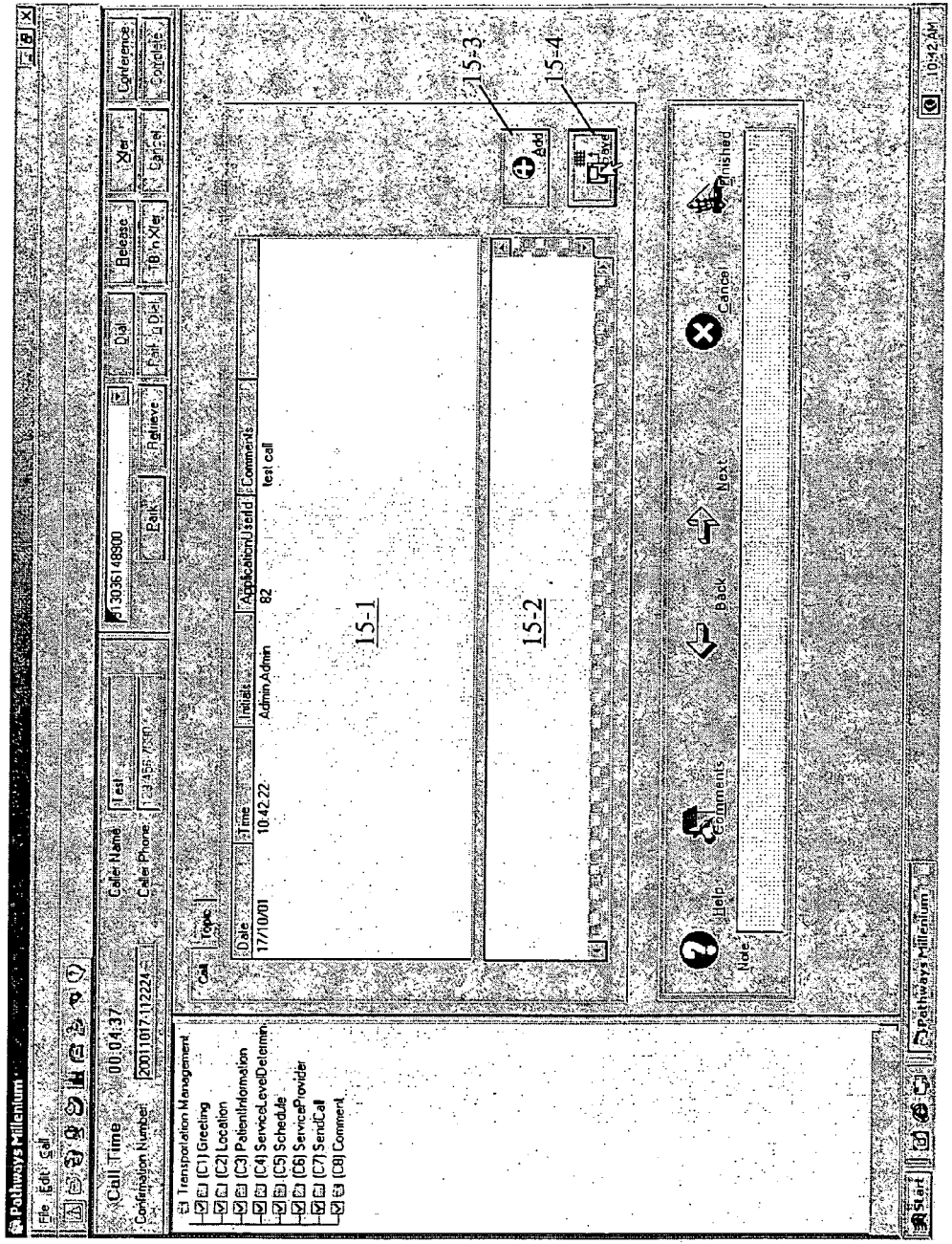
FIG. 15 is a view of a graphical user interface displayed by a comments module of the preferred embodiment.

FIG. 15 shows the user interface presented for the comments module in accordance with the preferred embodiment. The comments module enables the agent to record information concerning a call. Typically the agent uses this module to record information that is not reflected in the information captured by the other modules during the call.

The user interface includes a call form that includes a call box 15-1 and a text box 15-2. The call box 15-1 presents the comments already recorded for the current call. The comments are presented in a display-only grid format and arranged by module. The agent is enabled to enter further comments in the text box 15-2. An add button 15-3 enables the agent to add the entered text to the record for the call, and a save button 15-4 enables the agent to save any entered comments in the call record.

Reference ID Generation

The send call module generates a unique alphanumeric reference ID string for each call handled by the call center based on the data captured for the call. In the preferred embodiment the first seven characters of the reference ID represent features of the call and its disposition, and a predetermined number of additional characters are randomly generated and concatenated with the first seven characters to yield a unique reference ID. The first seven characters of the reference ID in the preferred embodiment are used to represent the following information:

| Character | Call Feature |
|---|---|
| 1 | Call source |
| 2 | Call source |
| 3 | Eligibility determination |
| 4 | Original Disposition |
| 5 | Final Disposition |
| 6 | Reason for disposition change |
| 7 | Final transaction classification |

The characters of the reference ID are generated as each of the relevant information items are determined by the system. In the event that a call is canceled, the reference number for the call is regenerated with the value X in the fourth through seventh characters. Reference ID characters are also regenerated in the event that the call source, patient information, final disposition or service provider for the call is changed. A final reference ID is generated when the call center agent marks the verify check box of the send call module to indicate oral confirmation by a transportation service provider, or when electronic confirmation is received by the system.

Quality Assurance Record Generation

To facilitate review of call center agent performance, a quality assurance record for each call is generated. The record includes a time stamp log generated by a time stamp module for each call. The time stamp log comprises time stamp data that can later be analyzed to characterize the efficiency and accuracy with which the call was handled by the call center agent. In the preferred embodiment, time stamp data is generated upon the occurrence of each of the following events:

Initial display of the greeting module
Initial keystroke by the agent in the greeting module
Placing of a call on hold
Removing a call from hold
Initial launch of the MTA or diagnostic application service level protocol
Completion of MTA or diagnostic application service level protocol
Agent acceptance of an original or changed disposition
Agent initiation of disposition change
Operation of send call button
Operation of close call button
Initiation of call to service provider
Receipt of CAD acknowledgement
Invocation of a new module
Closing of a module The quality assurance record also includes all entries and re-entries made in each field of the user interfaces.

Managed Transportation Application (MTA)

As described above, the MTA of the preferred embodiment perform five basic tasks: determination of an appropriate level of service, response time and response interval; determination of an original transaction classification for a transportation request; determination of the caller's authorization to change a service level or response time previously determined by the MTA; determination of a final transaction classification where the service level or response time was changed; and, determination of appropriate transportation providers for the requested transportation in accordance with applicable business rules.

As illustrated in FIG. 3, the MTA 3-11 utilizes a rules engine 3-12 to perform each of these services through the application of service level rules and business rules to data that is captured by the call management application 3-10 and modules 3-1 through 3-8 and that is stored in a call record maintained in the database 3-13. In the preferred embodiment the operation of the managed transportation application is connectionless with respect to the other system elements that it services. In other words, the MTA provides output data based on a set of input data without establishing a session that is specific to a particular call and without otherwise retaining knowledge of the call being serviced. For example, in the case of a request by the service level determination module for a service level determination, a set of data representative of information captured for the present call is provided to the MTA, and rules are applied to that data by the rules engine. If a service level determination is possible based on the data provided, that service level determination is returned to the service level determination module. On the other hand, if a service level determination is not possible, the MTA returns a question to the service level determination module. The question that is returned is associated with a particular service level determination rule that was unable to be applied due to the insufficiency of the data, and so that question is presented to the agent as described above with respect to FIGS. 10a-10e. Thus it is typical for the MTA to perform several iterations in this manner before a determination is obtained.

MTA Service Level Determination

The service level determination provided by the MTA is based on the application of service level rules to information concerning the patient's diagnoses, and, in most instances, to further information concerning the patient's equipment and medication needs. The service level rules are stored in dynamic rules tables, including a diagnosis rules table, an equipment rules table, and a medication rules table. In the preferred embodiment, the dynamic rules of the rules tables are supplemented by special service level rules that are used to implement exceptions to the rules of the service level rules tables.

FIG. 16 shows an excerpt from a diagnosis rules table employed in the preferred embodiment. As seen in FIG. 16, each rule associates a diagnosis with a severity level selected from a predetermined set of severity levels. For example, the first rule of the diagnosis rules table expresses the following relationship:

IF diagnosis is Abdominal Aortic Aneurysm THEN severity level is Very Acute

In the preferred embodiment, the severity levels, in order of greatest severity, are: 911, very acute, acute, non-acute and chronic. The severity levels associated with diagnoses may be used to abort the generation of further questions related to service level determination. For example, a diagnosis of cardiac arrest may be assigned a severity level of 911, and an MTA special rule may be provided to automatically assign a 911 service level without generating further questions when a severity level of 911 is encountered. The severity level is also used as a variable by further rules employed for determining a response time (discussed below).

The rules of the diagnosis rules table also associate each diagnosis with a diagnosis code. The diagnosis code of a selected diagnosis is stored with the call record and may be used as input to special diagnosis rules or to other rules in further iterations of the service level determination process.

One type of special diagnosis rule used in the preferred embodiment concerns patients with psychiatric diagnoses. The psychiatric rules require additional information concerning whether the patient is on hold, whether the patient is violent, and, in some cases, whether and how the patient is restrained. For example, one of the special psychiatric rules expresses the following relationship:

IF Primary Diagnosis is Psych AND (patient is Violent OR patient is On Hold) AND patient is Physically Restrained THEN Level of Service is BLS.

Other types of special diagnosis rules may involve other variables such as state, county or city, or a particular facility involved in the transportation.

FIG. 17 shows an excerpt from an equipment rules table of the preferred embodiment. The equipment rules table shows levels of service associated with various types of equipment that may be required during transportation. For example, the table expresses the following rule for an arterial sheath:

IF Equipment is Arterial Sheath THEN Level of Service is CCT

The rules of the equipment rules table also associate each equipment type with an equipment type code. The equipment type code of a selected equipment type is stored with the call record and may be used as input to special equipment rules or to other rules in further iterations of the service level determination process.

One type of special equipment rule modifies the outcome provided by the equipment rules table based on regulations that are applicable at the location of the patient. The following rule applies a California regulation concerning the service level required where a ventilator is used:

IF Reference ID is N* (in Call Source Table) AND Equipment is Ventilator/VBM THEN Level of Service is CCT In the aforementioned rule, N* is a value corresponding to a character from within the reference ID character string generated for the call (discussed below) that indicates that the call source is northern California.

The following rule applies an Oregon regulation concerning the level of service required where a tracheal device is used:

IF Response Location State is Oregon AND Equipment if Tracheal Device and Level of Service (from any other equipment) is NOT CCT then Level of Service is ALS Further special rules may be implemented to determine whether the present information concerning the patient's needs is sufficient to determine a level of service. The following is an example of such a rule:

IF Equipment indicates Level of Service is CCT THEN Level of Service is CCT.

This rule establishes that if the patient's equipment requires a CCT level of service, then the level of service must be CCT irrespective of any other factors. In such instances it becomes unnecessary to receive further input regarding, for example, the patient's medication needs.

Another rule may be used to establish the circumstances under which a patient's equipment needs are not determinative of service level:

IF Level of Service (from equipment table) is NOT CCT THEN go to medications table.

This rule establishes that if a service level associated with a patient's specific equipment needs is less then CCT, then the patient's medication needs must be determined before a service level determination is possible. Where this rule is applicable, the MTA returns a question to the service level determination module, causing the agent to be prompted for further input concerning the patient's medication needs.

An excerpt of a medications rules table of the preferred embodiment is shown in FIG. 18. The medications rules associate medications with levels of service that may depend on the manner of administration. For example, it may be seen in FIG. 18 that where the medication Adensosine is required by a patient, the appropriate level of service is variable, depending upon the manner of administration. Thus, the use of an IV push requires advanced life support (ALS), whereas the use of an IV pump or IV drip requires critical care transport (CCT). As a result, if the data captured for a call indicates that the patient needs Adensosine, but the manner of administration has not been specified, the MTA is unable to determine a level of service because the rule for Adensosine requires information concerning the manner of administration in order to determine a level of service. This is an instance in which the MTA returns a question concerning the manner of administration. In contrast, the medication rules indicate that where the patient requires the medication Amrinone, the level of service required is CCT irrespective of the manner of administration, and where the patient requires the medication Antibiotics, this type of medication has no effect on the service level determination.

The rules of the medications table are also supplemented by special rules. One type of special medications rule establishes exceptions to the rules contained in the medication rules table. The following is an example of a rule that alters the outcome provided by the medication rules table:

IF three or more Medications are being delivered AND they are all ALS THEN Level of Service is CCT.

This rule establishes a higher level of service than is provided by the rules tables when three or more medications requiring ALS service are required.

Another type of special rule resolves conflicts among different service levels required for different medications:

IF more than one medication is selected THEN the highest Level of Service must be used.

This rule establishes that if multiple medications are required, the medication requiring the highest level of service determines the level of service required based on the patient's medication needs.

Other special medication rules may involve other variables such as the state or county in which transportation occurs.

Additional special rules are implemented in addition to the types described above. The following special rule establishes that transportation is not authorized based on the information used to make the service level determination:

IF Level of Service is not determined THEN Level of Service is Not Authorized.

The preferred embodiment includes further special rules for producing desired outcomes under particular circumstances. Examples of the factors accounted for by other types of special rules include: bed confinement; infectious disease; patient size; patient age; response location; medical testing needs; medical necessity (where no other reason for transport has been given); and need for orthopedic devices.

MTA Response Time and Response Interval Determination

The MTA's service level determination is accompanied by determinations of an appropriate response time and an associated response interval. The responses and associated response intervals of the preferred embodiment are as follows:

| Response Time | Corresponding Response Interval |
| --- | --- |
| 911 | 911 |
| Urgent | 30 minutes |
| Immediate | 60 minutes |
| Scheduled | >60 minutes and <240 minutes |
| Prescheduled | =>240 minutes |
| Repatriation | 60 minutes |
| Team transport | 45 minutes OR 75 minutes OR 90 minutes |

A "team transport" response time indicates that the transportation includes picking up or dropping off persons in addition to the patient, such as a physician or nurse. Thus, in the case of the "team transport" response time, the response interval may be any one of three values depending on various factors.

The response time is a contractually defined performance parameter used in the preferred embodiment. The response time that is contractually mandated for a given transportation request may depend on a number of factors including the facility type of the response location, the response area within that facility, the facility type of the destination location, the destination area within that facility, the diagnosis severity level (determined using the diagnosis rules table previously described), and the original transaction-classification. The response time and its corresponding response interval are determined through the application of business rules that represent the contractual provisions for determining response time and response interval based on those factors. An excerpt from a response time rules table of the preferred embodiment is shown in FIG. 19. The response time rules associate combinations of the above factors with the response times shown in the right hand column. In cases where there are multiple diagnoses, the response time rules are applied to the diagnosis with the highest severity level.

In the preferred embodiment, special rules are provided to establish exceptions to the rules of the response time rules table based on regulations applicable at the location of transport. For example, the following rule implements a California regulation that affects the response interval:

IF Level of Service is CCT AND the Response Location State is NOT California and the Response Time Description is Immediate THEN Response interval is 90

Other special rules set up default response times for exceptional cases:

IF Response Time Description is not determined THEN Response Time Description is Prescheduled MTA Original Transaction Classification The MTA of the preferred embodiment provides an original transaction classification based on the service level that is determined by the system for the requested transportation. The original transaction classification is a determination of responsibility for the cost of transportation, which may in some instances include a determination of how the cost is determined (e.g. fixed fee vs. at cost). This determination is based on the contractual provisions that account for factors concerning the circumstances of the transportation, and therefore the determination is made through the application of transaction classification business rules to information describing the transportation. The information to which the transaction classification rules are applied includes patient eligibility status, facility type, plan type of the facility, whether the facility is owned, contracted or non-contracted (i.e. the relationship between the facility and the client on whose behalf the call center is acting), and the level of service determined by the system through the application of service level rules as previously described. In the preferred embodiment the following transaction classifications are used: scheduled (paid by the patient's insurer at a predetermined contract rate based on the level of service and response time); nonscheduled (a transport request not covered by the agreements among the patient, insurer and transportation provider); nonscheduled 911; not authorized (the insurer does not authorize the transportation); patient pay (the patient is responsible for the cost of transportation); hospice; and nontransport.

The preferred embodiment employs three types of rules in the MTA transaction classification determination. FIG. 20 shows an excerpt of a facility type rules table of the preferred embodiment used by the MTA for transaction classification determination. These rules represent contractual provisions for allocating responsibility for payment based on the type of facility from which the transportation originates and the type of the destination facility. The facility type rules output either a transaction class, an instruction to use further business rules that determine a transaction classification based on the level of service, or an instruction to run rules contained in a plan type rules table. FIG. 21 shows an excerpt of a plan type rules table of the preferred embodiment. The plan type rules represent contractual provisions for allocating responsibility for payment based on the plan type and contract type of the response location and destination location and output either a transaction class (e.g. nonscheduled) or an instruction to use further business rules that determine a transaction classification based on the level of service.

MTA Original Disposition Change Authorization

Once an original disposition (a level of service, response time and response interval) has been determined, the call center agent is enabled to accept or reject it. An agent may choose to reject an original disposition, for example, where the agent realizes that one or more questions relating to the original disposition were answered incorrectly, resulting in an erroneous original disposition. A caller may also wish to reject an original disposition, such as for clinical or operational reasons. For example, the caller may wish to reject an original disposition and seek an upgrade or downgrade of the service level or response time, or override a determination that the transportation is not authorized. The authority of the caller to authorize a change in the original disposition is dictated by contractual provisions governing the request for transportation. Accordingly, the determination of authority to authorize a change in the original disposition is made by applying disposition change authorization business rules representing those contractual provisions to information relating to the transportation request and the desired change. In the preferred embodiment, the information considered by the disposition change authorization rules includes the facility from which the call is received, the type of caller (physician, RN, etc.), affiliation with a particular health plan that grants special permission for certain types of callers to modify the original disposition, the desired new level of service, the response time or response interval, and the reason for requesting the change. FIG. 22 shows an excerpt of an disposition change authorization rules table of the preferred embodiment. The rules yield a yes or no answer regarding whether the caller is authorized to change the original disposition determined by the system.

To change an original disposition, the caller must provide the desired new level of service, response time or response interval. The caller must also provide a reason for changes in the service level or response time. This information is used in the final transaction classification determination as discussed below. In the preferred embodiment, the caller must select such change reasons from a predefined set of change reasons corresponding to change reasons used in the final transaction classification rules. The predefined level of service change reasons of the preferred embodiment are: physician (clinical), registered nurse (clinical), call center agent, call center supervisor, non-clinician administrator (client), patient pay per client, patient/caller, third party clinical (non-client), third party admin (non-client), and no upgrade requested. The predefined response time change reasons of the preferred embodiment are: clinical condition, call center agent, client MD request, client RN request, client request, and no change requested.

MTA Final Transaction Classification Determination

The MTA is invoked automatically to determine a final transaction classification (i.e. a final determination of responsibility for payment) based on the original disposition and any requested changes. This determination of responsibility is governed by contractual provisions and therefore the final transaction classification determination is made by applying business rules representing the governing contractual provisions to relevant information. FIG. 23 shows an excerpt of a final transaction classification rules table of the preferred embodiment. The final transaction classification rules determine a final transaction classification and final transaction classification change type based on information concerning the original transaction classification, any level of service change, the change reason provided for any level of service change, any response time description change, the response time change reason, and any response interval change. In the preferred embodiment the following final transaction classifications are used: scheduled downgrade, scheduled override, scheduled upgrade, scheduled, nonscheduled, nonscheduled 911, not authorized, patient pay, hospice, non-transport, authorized leakage, and authorized 911 (leakage). The classification change types of the preferred embodiment are: leakage, correction, level of service override/response time upgrade, level of service downgrade, level of service downgrade/response time downgrade 911, level of service downgrade/response time upgrade 911, level of service downgrade/response time downgrade, level of service downgrade/response time upgrade, level of service override, level of service override/response time downgrade, level of service upgrade, level of service upgrade/response time downgrade, level of service upgrade/response time downgrade 911, level of service upgrade/response time upgrade, level of service upgrade/response time upgrade 911, no change, response time downgrade, response time downgrade 911, response time upgrade, and response time upgrade 911.

Additional special rules may be provided to implement exceptions to the rules of the final transaction classification rules table as necessary.

MTA Service Provider Determination

The MTA determines available transportation providers for a given call based on the information obtained during the course of the call. These determinations are made by the application of special rules and typically involve a determination based on one or more of the following types of information: response location state; response location county; response area; response location (name of location where patient is located); call source code; eligibility code; service level; and response time description. These rules account for differences in availability of services in different locations. For example, in some locations, some transportation providers may only provide critical care and advanced life support services, while others only provide basic life support services. Similarly, some providers may provide only pre-scheduled transportation.

In the preferred embodiment, three types of search results are generated to produce a list of service providers. The first generates a default provider that is determined based on the level of service and the call source. The following is an example of a rule of this type in the preferred embodiment:

IF the Response Location State is Oregon AND Response Location City is Springfield THEN the Recommended Service Provider is Springfield Fire The second of search generates providers based on the level of service and a geographic search that sequentially searches by zip code, then city (if the "within city limits" box has been checked in the location module user interface), then county, until one or more providers are identified. The third generates providers by applying business rules representing contractual provisions governing the use of particular transportation providers. For example, a business rule may dictate that under certain circumstances the request must be dispatched to a specific provider, or that under certain circumstances the least expensive of the available providers is listed as the first choice.

Alternative Implementations

The preferred embodiment described herein is adapted for providing service level determinations and business rule determinations in accordance with regulations and contracts applicable to regions and parties presently served by the preferred embodiment. However it should be understood that the preferred embodiment merely represents one implementation of a system in accordance with the invention. The invention is not limited to the system architecture, call process flow or user interfaces disclosed herein. Rather, a variety of alternative architectures, process flows and user interfaces may be implemented in accordance with the regions and contracting parties for which service level determinations and determinations of responsibility for payment are to be made.

What is claimed is:

1. An apparatus for managing requests for medical transportation, comprising:
   a processor configured to execute instructions stored in computer-readable media;
   at least one non-transitory computer readable media having stored thereupon a plurality of service level rules, the service level rules expressing associations between service levels of medical transportation and patient diagnoses, patient equipment needs during transportation, and patient medication needs during transportation;
   the at least one non-transitory computer readable media further having stored thereupon a plurality of business rules, the business rules including rules expressing associations between locations of transportation, rules representing contractual provisions governing responsibility for a cost of requested transportation, and contractual transportation performance standards comprising response times for providing requested transportation;
   an interface, running on the processor, for receiving, at the apparatus, a first request for transportation;
   a rules engine, running on the processor and configured to receive the first request from the interface and to access the at least one non-transitory computer readable media, the rules engine being configured to, prior to a dispatch of transportation associated with the received first request, cause the processor to:
   (1) apply said service level rules to details of the received first request for transportation, to determine a service level for said requested transportation,
   (2) apply said business rules to the details of the received first request to determine performance standards for the requested transportation, and
   (3) apply said business rules to details of the received first request to determine responsibility for a cost of the requested transportation; and
   wherein the apparatus further comprises a module configured to cause a second request for transportation to be dispatched from the apparatus based on the service level and performance standards determined by the rules engine.

2. The apparatus claimed in claim 1, wherein said business rules governing responsibility for the cost of said requested transportation operate on information including at least one of patient eligibility status, a type of a facility from which the requested transportation originates, a type of a destination facility of the requested transportation, a relationship between the facility and an insurer of the patient, and a level of service determined for the requested transportation.

3. The apparatus claimed in claim 1, wherein said business rules further include rules representing contractual provisions governing authority of requesting parties to change at least one of a level of service and a performance standard determined by the system for the requested transportation, and
   wherein the rules engine applies said business rules to information relating to said requested transportation to determine authority of a requesting party to change at least one of a level of service and a performance standard determined by the system for the requested transportation.

4. The apparatus claimed in claim 3, wherein said business rules representing authority of requesting parties to change a level of service determined by the system for the requested transportation operate on information including at least one of a type of a facility from which the request is made, a type of the requester, affiliation of the requester with an insurer that grants permission for the requester to modify the service level, a desired new service level, a desired new response time, and a reason for requesting the change.

5. The apparatus claimed in claim 3, wherein said business rules further include rules representing contractual provisions governing responsibility for a cost of requested transportation upon approval of a requested change of at least one of a service level and a performance standard determined by the system for requested transportation, and
   wherein the rules engine applies said business rules to information relating to said requested transportation to determine responsibility for the cost of the requested transportation upon approval of a requested change of at least one of a service level and a performance standard determined by the system for the requested transportation.

6. The apparatus claimed in claim 5, wherein said business rules representing contractual provisions governing responsibility for a cost of said requested transportation upon approval of a requested change of at least one of a service level and a performance standard operate on information including at least one of an original determination of responsibility for cost of the requested transportation, a type of change of service level, a reason for change of service level, a type of change of response time, and a reason for change of response time.

7. The apparatus claimed in claim 1, wherein said business rules further include rules representing contractual provisions governing selection of a transportation provider for requested transportation, and
   wherein the rules engine applies said business rules to information relating to said requested transportation to determine one or more transportation providers for providing the requested transportation in accordance with said contractual provisions governing selection of a transportation provider for requested transportation.

* * * * *